(12) United States Patent
Folkman et al.

(10) Patent No.: US 8,273,383 B2
(45) Date of Patent: Sep. 25, 2012

(54) METHODS AND COMPOSITIONS FOR TREATMENT OF PREECLAMPSIA

(75) Inventors: Judah Folkman, Brookline, MA (US); Raghu Kalluri, Weston, MA (US)

(73) Assignees: Children's Medical Center Corporation, Boston, MA (US); Beth Israel Deaconess Medical Center, Boston, MA (US)

( * ) Notice: Subject to any disclaimer, the term of this patent is extended or adjusted under 35 U.S.C. 154(b) by 546 days.

(21) Appl. No.: 11/579,777

(22) PCT Filed: May 4, 2005

(86) PCT No.: PCT/US2005/015511
§ 371 (c)(1),
(2), (4) Date: Oct. 2, 2007

(87) PCT Pub. No.: WO2005/110462
PCT Pub. Date: Nov. 24, 2005

(65) Prior Publication Data
US 2008/0160105 A1    Jul. 3, 2008

Related U.S. Application Data

(60) Provisional application No. 60/567,981, filed on May 4, 2004.

(51) Int. Cl.
*A61K 31/56* (2006.01)
(52) U.S. Cl. .................. 424/682; 514/171; 514/182
(58) Field of Classification Search .................. 424/682; 514/171, 182
See application file for complete search history.

(56) References Cited

U.S. PATENT DOCUMENTS

| | | | |
|---|---|---|---|
| 4,963,590 A | 10/1990 | Backstrom et al. | |
| 5,194,596 A | 3/1993 | Tischer et al. | |
| 5,219,739 A | 6/1993 | Tischer et al. | |
| 5,238,819 A | 8/1993 | Roberts et al. | |
| 5,240,848 A | 8/1993 | Keck et al. | |
| 5,332,671 A | 7/1994 | Ferrara et al. | |
| 5,543,138 A | 8/1996 | Keith | |
| 5,643,900 A | 7/1997 | Fotsis et al. | |
| 5,712,395 A | 1/1998 | App et al. | |
| 5,739,302 A * | 4/1998 | Suzuki et al. | 536/5 |
| 5,763,441 A | 6/1998 | App et al. | |
| 5,830,879 A | 11/1998 | Isner | |
| 5,895,783 A | 4/1999 | Garfield et al. | |
| 5,958,715 A | 9/1999 | Muller | |
| 6,100,071 A | 8/2000 | Davis-Smyth et al. | |
| 6,258,787 B1 | 7/2001 | Isner | |
| 6,365,157 B2 | 4/2002 | Rockwell et al. | |
| 6,399,585 B1 | 6/2002 | Larson et al. | |
| 6,410,322 B1 | 6/2002 | Robinson | |
| 6,447,768 B1 | 9/2002 | Van Zonneveld et al. | |
| 6,528,676 B1 | 3/2003 | D'Amato et al. | |
| 6,613,757 B1 | 9/2003 | Garfield et al. | |
| 6,660,534 B2 | 12/2003 | McVicker et al. | |
| 6,677,300 B1 | 1/2004 | Schreiner et al. | |
| 7,030,083 B2 | 4/2006 | Schreiner et al. | |
| 7,323,346 B2 | 1/2008 | Thadhani et al. | |
| 7,335,362 B2 | 2/2008 | Karumanchi et al. | |
| 7,344,892 B2 | 3/2008 | Thadhani et al. | |
| 7,407,659 B2 | 8/2008 | Karumanchi et al. | |
| 7,425,419 B2 | 9/2008 | Poston et al. | |
| 7,435,419 B2 | 10/2008 | Karumanchi et al. | |
| 7,727,733 B2 | 6/2010 | Buhimschi et al. | |
| 7,829,573 B2 | 11/2010 | Curwen et al. | |
| 7,846,433 B2 | 12/2010 | Karumanchi et al. | |
| 2001/0056068 A1 | 12/2001 | Chwalisz et al. | |
| 2002/0082433 A1 | 6/2002 | Agoston et al. | |
| 2002/0147183 A1 | 10/2002 | Agoston et al. | |
| 2003/0114412 A1 | 6/2003 | Ward et al. | |
| 2006/0172943 A1 * | 8/2006 | Edelberg et al. | 514/12 |

FOREIGN PATENT DOCUMENTS

| | | |
|---|---|---|
| CA | 1302418 C | 6/1992 |
| EP | 0237929 B1 | 6/1993 |
| EP | 1 417 971 A2 | 5/2004 |
| GB | 2200109 A | 7/1988 |
| WO | 96/37456 A1 | 11/1996 |
| WO | 98/28006 A1 | 7/1998 |
| WO | 02/37120 A2 | 5/2002 |
| WO | 2005/023197 A3 | 3/2005 |
| WO | 2005/110462 A3 | 11/2005 |
| WO | 2006/069373 A2 | 6/2006 |

OTHER PUBLICATIONS

Cushman et. al. (J. Med. Chem. (1995) 38:2041-2049).*
McCoy et. al. (Am. J. Health-Syst. Pharm. (2009) 66:337-344).*
Tron et. al. (J. Med. Chem. (2006) 49:3033-3044).*
Lindheimer et. al. (Annual review of Medicine (1989) 40:233-250).*
Takanashi et. al. (Biol. Pharm. Bull. (1995) 18:1120-1125).*
Tofovic et. al. (Journal of the American Society of Nephrology (2003) 14:620A (abstract)).*
Takanashi (Lipids (2003) 38:847-854).*
Luttun et. al. (Journal of Clinical Investigation (2003) 111:600-602).*
Khong, T.Y. et al. Br. J. Obstet. Gynecol., 93:1049-1059 (1986).
Roberts, J.M. et al., Am. J. Hypertens., 4:700-708 (1991).
Robertson, W.B. et al., Am J. Obstet. Gynecol., 155(2):401-412 (1986).
Acien, P. et al., International Journal of Gynecology and Obstetrics, 32(3):229-235 (1990). "Perinatal morbidity and mortality in pregnancy hypertensive disorders: prognostic value of the clinical and laboratory findings."

(Continued)

*Primary Examiner* — Marcos Sznaidman
(74) *Attorney, Agent, or Firm* — Nixon Peabody LLP; David S. Resnick; Shayne Y. Huff

(57) ABSTRACT

Methods and compositions for treating and/or preventing a pregnancy related disease or disorder are provided. The methods involve administration of 2-methoxyestradiol, or an analog thereof, to a subject. Also provided are methods for diagnosing or predicting a pregnancy related disease or disorder. The methods involve detection of 2-methoxyestradiol, or a precursor or metabolite thereof.

33 Claims, 7 Drawing Sheets

OTHER PUBLICATIONS

Bhansali, K.G. et al., Database Medline [Online], U.S. National Library of Medicine, 1992, XP002531982. "Quantitative determination of 17 beta-estradiol and progesterone in cellular fractions of term placentae of normal and hypertensive patients."

Mizutani, S. et al., Experimental and Clinical Endocrinology, 92(2)161-170 (1988). "Positive effect of estradiol and progesterone in severe preeclampsia."

Mooberry, S.L., Drug Resistance Updates: Review and Commentaries in Antimicrobial and Anticancer Chemotherapy, 6(6):355-361 (2003). "Mechanism of action of 2-methoxyestradiol: new developments."

Nadar, S. et al., American Journal of Hypertension, 17(5):S161-S162 (2004). "Plasma markers of angiogenesis in pregnancy induced hypertension."

Svedas, E. et al., American Journal of Obstetrics and Gynecology, 187(6):1608-1616 (2002). "Endothelial dysfunction in uterine circulation in preeclampsia: Can estrogens improve it?"

Takanashi, K., Database Medline [Online], U.S. National Library of Medicine, 2003, XP002531983. "Studies on 2-hydroxyestradiol 17-sulfate derived from fetoplacental unit: the antioxidant as a potential defense substance against preeclampsia."

Zeisler, H. et al., Wiener Klinische Wochenschrift, 114(12):458-461 (2002). "Concentrations of estrogens in patients with preeclampsia."

Ahmad, S. et al., "Elevated placental soluble vascular endothelial growth factor receptor-1 inhibits angiogenesis in preeclampsia," Circ. Res. 95:884-891 (2004).

Barnea, E.R. et al. "Catechol-O-methyltransferase activity in the human term placenta," American Journal of Perinatology, Thieme-Stratton, New York, NY, US 5(2):121-127 (1988).

Bates, G.W. et al., "Erythrocyte catechol-O-methyltransferase activity in pregnant women with prenancy-induced hypertension", American Journal of Obstetrics & Gynecology, Mosby, St. Louis, MO, US 142(2):177-178 (1982).

Bennedsen, B.E. et al., "Obstetric complications in women with schizophrenia," Schizophr. Res. 47:167-175 (2001).

Nadar, S. et al., "Plasma markers of angiogenesis in pregnancy induced hypertension," Thromb Haemost 94:1071-1076 (2005).

Casey, M.L. et al., "Characterization of catechol-O-methyltransferase activity in human uterine decidua vera tissue," Am. J. Obstet. Gynecol. 145:453-457 (1983).

Chen, C. et al., Systematic Mutation Analysis of the Catechol O-Methyltransferase Gene as a Candidate Gene for Schizophrenia, Am. J. Psychiatry 156:1273-1275 (1999).

Chen, J. et al., "Functional Analysis of Genetic Variation in Catechol-O-Methyltransferase (COMT): Effects on mRNA, Protein, and Enzyme Activity in Postmortem Human Brain," Am. J. Hum. Genet. 75:807-821 (2004).

Cotton, N.J.H. et al., Oxidative Inhibition of Human Soluble Catechol-O-Methyltransferase, J. Biol. Chem. 279:23710-23718 (2004).

Gogos, J.A. et al., "Catechol-O-methyltransferase-deficient mice exhibit sexually dimorphic changes in catecholamine levels and behavior," Proc. Natl Acad. Sci. USA 95:9991-9996 (1998).

Kendell, R.E., "Obstetric Complications and Schizophrenia: A Case Control Study Based on Standardized Obstetric Records," British J. Psychiatry 168:556-561 (1996).

Kirov, G. et al., Low Activity Allele of Catechol-O-Methyltransferase Gene Associated with Rapid Cycling Bipolar DisorderMol. Psychiatry 3:342-345 (1998).

Levine, R.J. et al., "Circulating angiogenic factors and the risk of preeclampsia," N. Engl. J. Med. 350:672-683 (2004).

Maynard, S.E. et al. "Excess placental soluble fms-like tyrosine kinase 1 (sFlt1) may contribute to endothelial dysfunction, hypertension, and proteinuria in preeclampsia," J. Clin. Invest. 111:649-658 (2003).

Nagamatsu, T. et al. "Cytotrophoblasts up-regulate soluble fms-like tyrosine kinase-1 expression under reduced oxygen: an implication for the placental vascular development and the pathophysiology of preeclampsia," Endocrinology 145(11):4838-4845 (2004).

Sun et al, "Association between catechol-methyltransferase gene polymorphism and pregnancy induced hypertension", Database Medline [Online] US National Library of Medicine (NLM), Bethesda, MD, US, Accession No. NLM14989982, Abstract. XP-002568262.

Aggarwal et al., "Low Urinary Placental Growth Factor is a Marker of Preeclampsia," Kidney Int. 69(3): 621-624 (2006).

Ahmed et al., "Regulation of Placental Vascular Endothelial Growth Factor (VEGF) and Placenta Growth Factor (PIGF) and Soluble Flt-1 by Oxygen—A Review," Placenta 21:S16-S24 (2000).

Barleon et al., "Soluble VEGFR-1 Secreted by Endothelial Cells and Monocytes is Present in Human Serum and Plasma from Healthy Donors," Angiogenesis 4:143-154 (2001).

Baumweli et al., "Preeclampsia: Clinical Manifestations and Molecular Mechanisms," Nephron. Clin. Pract. 106(2): c72-81 (2007).

Bdolah et al., "Angiogenic Imbalance in the Pathophysiology of Preeclamsia: Newer Insights," Semin. Nephrol. 24(6): 548-556 (2004).

Bdolah et al., "Recent Advances in Understanding of Preeclampsia," Croat. Med. J. 46(5): 728-736 (2005).

Belgore et al., "Measurement of Free and Complexed Soluble Vascular Endothelial Growth Factor Receptor, Flt-1, in Fluid Samples: Development and Application of Two New Immunoassays," Clin. Sci. 100:567-575 (2001).

Belgore et al., "sFlt-1, a Potential Antagonist for Exogenous VEGF," Circulation 102:E108-109 (2000).

Belgore et al., "Successful Therapy Reduces Levels of Vascular Endothelial Growth Factor (VEGF) in Patients with Hypertension and Patients with Hypercholesterolemia," Atherosclerosis 151: 599 (2000).

Belgore et al., "Vascular Endothelial Growth Factor and its Receptor, Flt-1, in Smokers and Non-Smokers," Br. J. Biomed. Sci. 57: 207-213 (2000).

Bolte et al., "Management and Monitoring of Severe Preeclampsia," Eur. J. Obstet. Gynecol. Reprod. Biol. 96: 8-20 (2001).

Brockelsby et al., "VEGF Via VEGF Receptor-1 (Flt-1) Mimics Preeclamptic Plasma in Inhibiting Uterine Blood Vessel Relaxation in Pregnancy: Implications in the Pathogenesis of Preeclampsia," Lab. Invest.79: 1101-1111 (1999).

Brown et al., "Vascular Permeability Factor mRNA and Protein Expression in Human Kidney," Kidney Int. 42: 1457-1461 (1992).

Carmeliet et al., "Synergism between vascular endothelial growth factor and placental growth factor contributes to angiogenesis and plasma extravasation in pathological conditions," Nat. Med. 5: 575-583 (2001).

Carr et al., "Hemodynamically-Directed Atenolol Therapy is Associated With a Blunted Rise in Maternal sFLT-1 Levels During Pregnancy," Hypertens. Pregnancy 28(1): 42-55 (2008).

Celletti et al., "Effect of Human Recombinant Vascular Endothelial Growth Factor 165 on Progression of Atherosclerotic Plaque," J. Am. Coll. Cardiol. 37: 2126-2130 (2001).

Charnock-Jones et al., "Identification and Localization of Alternately Spliced mRNAs for Vascular Endothelial Growth Factor in Human Uterus and Estrogen Regulation in Endometrial Carcinoma Cell Lines," Biol. Reprod. 48: 1120-1128 (1993).

Clark et al., "A Vascular Endothelial Growth Factor Antagonist is Produced by the Human Placenta and Released into the Maternal Circulation," Biol. Reprod. 59: 1540-1548 (1998).

Cockell et al., "Human Placental Syncytiotrophoblast Microvillous Membranes Impair Maternal Vascular Endothelial Function," Br. J. Obstet. Gynaecol. 104: 235-240 (1997).

Cohen et al., "Circulating Levels of the Antiangiogenic Marker Soluble Fms-Like Tyrosine Kinase 1 Are Elevated in Women With Pregestational Diabetes and Preeclampsia: Angiogenic Markers in Preeclampsia and Preexisting Diabetes," Diabetes Care 30(2): 375-377 (2007).

Cooper et al., "VEGF mRNA levels in placentae from pregnancies complicated by pre-eclampsia," B. J. Obstet. Gynacol. 103: 1191-1196 (1996).

Davis-Smyth et al., "The Second Immunoglobulin-Like Domain of the VEGF Tyrosine Kinase Receptor Flt-1 Determines Ligand Binding and May Initiate a Signal Transduction Cascade," EMBO J. 15: 4919-4927 (1996).

Eremina et al., Glomerular-Specific Alterations of VEGF-A Expression Lead to Distinct Congenital and Acquired Renal Diseases. J. Clin. Invest. 111: 707-716 (2003).

Eskild et al., "Levels of Angiogenic Factors in Pregnancy and Post-Partum Bleeding," Acta. Obstet. Gynecol. Scand. 87(10): 1081-1083 (2008).

Ferguson, "Meeting Highlights: Highlights of the 48th Scientific Sessions of the American College of Cardiology," Circulation 100: 570-575 (1999).

Ferrara et al., "Role of Vascular Endothelial Growth Factor in the Regulation of Angiogenesis," Kidney Int. 56: 794-814 (1999).

Ferrara et al., "The Role of Vascular Endothelial Growth Factor in Angiogenesis," Acta Haematol. 106: 148-156 (2001).

Ferrara et al., "Role of Vascular Endothelial Growth Factor in Regulation of Physiological Angiogenesis," Am. J. Physiol. Cell Physiol. 280: C1358-C1366 (2001).

Ferrara et al., "The Biology of VEGF and Its Receptors," Nat. Med. 9: 669-676 (2003).

Germain et al., "Endothelial Dysfunction: A Link Among Preeclampsia, Recurrent Pregnancy Loss, and Future Cardiovascular Events?" Hypertension 49(1): 90-95 (2006).

Gille et al., "Analysis of Biological Effects and Signaling Properties of Flt-1 (VEGFR-1) and KDR (VEGFR-2)," J. Biol. Chem. 276: 3222-3230 (2001).

Hayashi et al., "Changes in Urinary Excretion of Six Biochemical Parameters in Normotensive Pregnancy and Preeclampsia," Am. J. Kidney Dis. 39: 392-400 (2002).

He et al., "Alternative Splicing of Vascular Endothelial Growth Factor (VEGF)-R1 (FLT-1) pre-mRNA is Important for the Regulation of VEGF Activity," Mol. Endocrinol. 13: 537-45 (1999).

He et al., Vascular Endothelial Growth Factor Signals Endothelial Cell Production of Nitric Oxide and Prostacyclin Through Flk-1/KDR Activation of c-Src. J. Biol. Chem. 274: 25130-21535 (1999).

Heeschen et al. "Nicotine Stimulates Angiogenesis and Promotes Tumor Growth and Atherosclerosis," Nat. Med. 7: 833-839 (2001).

Helske et al., "Expression of Vascular Endothelial Growth Factor Receptors 1, 2 and 3 in Placentas From Normal and Complicated Pregnancies," Mol. Hum. Reprod. 7: 205-210 (2001).

Hladunewich et al., "Pathophysiology of the Clinical Manifestations of Preeclampsia," Clin. J. Am. Soc. Nephrol. 2 (3): 543-549 (2007).

Holston et al., "Circulating Angiogenic Factors in Gestational Proteinuria Without Hypertension," Am. J. Obstet. Gynecol. (4) 392: e1-10 (2009).

Hornig et al., "Release and Complex Formation of Soluble VEGFR-1 from Endothelial Cells and Biological Fluids," Lab. Invest. 80: 443-454 (2000).

Hsieh, Tsang-Tang, "Maternal Serum Placenta Growth Factor and Vascular Endothelial Growth Factor in Pregnancies Complicated by Preeclampsia," Am. J. Obstet. Gynecol. 184: S70 (2001). (Abstract).

Hunter et al., "Serum Levels of Vascular Endothelial Growth Factor in Preeclamptic and Normotensive Pregnancy," Hypertension 36: 965-969 (2000).

Iyer et al., "The Crystal Structure of Human Placenta Growth Factor-1 (PlGF-1), an Angiogenic Protein, at 2.0 Å Resolution," J. Biol. Chem. 276: 12153-12161 (2001).

Kabbinavar et al., "Phase II, Randomized Trial Comparing Bevacizumab Plus Fluorouracil (FU)/leucovorin (LV) with FU/LV Alone in Patients with Metastic Randomized Colorectal Cancer," J. Clin. Oncol. 21: 60-65 (2003).

Karumanchi et al., "Advances in the Understanding of Eclampsia," Curr. Hypertens. Rep. 10(4): 305-312 (2008).

Karumanchi et al., "Preeclampsia Pathogenesis: "Triple a Rating"—Autoantibodies and Antiangiogenic Factors," Hypertension 51(4): 991-992 (2008).

Karumanchi et al., "Placental Ischemia and Soluble Fms-Like Tyrosine Kinase 1: Cause or Consequence of Preeclampsia?" Kidney Int. 71(10): 959-961 (2007).

Karumanchi et al., "Preeclampsia and The Kidney: Footprints in the Urine," Am. J. Obstet. Gynecol. 196(4): 287-288 (2007).

Karumanchi et al., "Preeclampsia: A Renal Prespective," Kidney Int. 67(6): 2101-2113 (2005).

Karumanchi et al., "Hypoxia and Sflt-1 in Preeclampsia: The "Chicken-and-Egg" Question," Endocrinology 145(11): 4835-4837 (2004).

Kendall et al., "Identification of a Natural Soluble Form of the Vascular Endothelial Growth Factor Receptor, FLT-1, and Its Heterodimerization with KDR," Biochem. Biophys. Res. Commun. 226: 324-328 (1996).

Kendall et al., "Inhibition of Vascular Endothelial Cell Growth Factor Activity by an Endogenously Encoded Soluble Receptor," Proc. Natl. Acad. Sci. 90: 10705-10709 (1993).

Keyt et al., "Indentification of Vascular Endothelial Growth Factor Determinants for Binding KDR and Flt-1 Receptors," J. Biol. Chem. 271: 5638-5646 (1996).

Koga et al., "Elevated Serum Soluble Vascular Endothelial Growth Factor Receptor 1 (sVEGFR-1) Levels in Women with Preeclampsia," J. Clin. Endocrinol. Metab. 88: 2348-2351 (2003).

Lain et al., "Contemporary Concepts of the Pathogenesis and Management of Preeclampsia," JAMA 287: 3183-3186 (2002).

Lam et al., "Circulating Angiogenic Factors in the Pathogenesis and Prediction of Preeclampsia," J. Hypertension 46 (5): 1077-1085 (2005).

Lash et al., "Vascular Endothelial Growth Factor and Placental Growth Factor Release in Cultured Trophoblast Cells Under Different Oxygen Tensions," Growth Factors 20(4):189-196 (2002).

Levine et al., "Trial of Calcium for Preeclampsia Prevention (CPEP): Rationale, Design, and Methods," Control Clin. Trials 17: 442-469 (1996).

Levine et al., "Trial of Calcium to Prevent Preeclampsia," N. Engl. J. Med. 337:69-76 (1997).

Levine et al., "Two-Stage Elevation of Cell-Free Fetal DNA in Maternal Sera Before Onset of Preeclampsia," Am. J. Obstet. Gynecol. 190: 707-713 (2004).

Levine et al., "Serum Sflt1 Concentration During Preeclampsia and Mid Trimester Blood Pressure in Healthy Nulliparous Women," Am. J. Obstet. Gynecol. 194(4): 1034-1041 (2006).

Li et al., "Recombinant VEGF121 Attenuates Hypertension and Improves Kidney Damage in a Rat Model of Preeclampsia," Hypertension 107: 092098 (2007).

Li et al., "Recombinant Vascular Endothelial Growth Factor 121 Attenuates Hypertension and Improves Kidney Damage in a Rat Model of Preeclampsia," Hypertension 50(4): 686-692 (2007).

Livingston et al., "Placenta Growth Factor is not an Early Marker for the Development of Severe Preeclampsia," Am. J. Obstet. Gynecol. 184: 1218-1220 (2001).

Livingston et al., "Reductions of Vascular Endothelial Growth Factor and Placental Growth Factor Concentrations in Severe Preeclampsia," Am. J. Obstet. Gynecol. 183: 1554-1557 (2000).

Luttun et al., "Soluble VEGF Receptor Flt1: The Elusive Preclampsia Factor Discovered?," J. Clin. Invest. 111: 600-602 (2003).

Lutton et al., "Revascularization of ischemic tissues by PlGF treatment, and inhibition of tumor angiogenesis, arthritis and atherosclerosis by anti-Flt1," Nat. Med. 8: 831-840 (2002).

Lyall et al., "Suppression of Serum Vascular Endothelial Growth Factor Immunoreactivity in Normal Pregnancy and in Pre-eclamsia," BJOG 104: 223-228 (1997).

Margolin et al., "Phase lb Trial of Intravenous Recombinant Humanized Monoclonal Antibody to Vascular Endothelial Growth Factor in Combination with Chemotherapy in Patients with Advanced Cancer: Pharmacologic and Long-Term Safety Data," J. Clin. Oncol. 19: 851-856 (2001).

Masuda et al., "Vascular Endothelial Growth Factor Enhances Glomerular Capillary Repair and Accelerates Resolution of Experimentally Induced Glomerulonephritis," Am. J. Pathol. 159: 599-608 (2001).

Maynard et al., "Sflt-1, a Circulating VEGF Antagonist, is Up-regulated in Preeclampsia and Contributes to Endothelial Dysfunction," J. Am. Soc. Nephrol. 13: SU-FC280 (2002).

Maynard et al., "Excess Placental Soluble fms-Like Tyrosine Kinase 1 (sFlt-1) May Contribute to Endothelial Dysfunction, Hypertension, and Proteinuria in Preeclampsia," J. Clinical Invest. 111: 649-658 (2003).

Maynard et al., "Soluble Fms-like Tyrosine Kinase 1 (sFlt1) and Endothelial Dysfunction in the Pathogenesis of Preeclampsia," Pediatr. Res. 57: 1R-7R (2005).

Maynard et al., "Preeclampsia and Angiogenic Imbalance," Annu. Rev. Med. 59: 61-78 (2008).

Mills et al., "Prostacyclin and Thromboxane Changes Predating Clinical Onset of Preeclampsia," JAMA 281: 356-362 (1999).

Morbidelli et al., "Nitric Oxide Mediates Mitogenic Effect of VEGF on Coronary Venular Endothelium," Am. J. Physiol. 270: H411-4115 (1996).

Mortensen et al., "Smoking, Sex of the Offspring, and Risk of Placental Abruption, Placenta Previa, and Preeclampsia: a Population-Based Cohort Study," Acta Obstet. Gynecol. Scand 80: 894-898 (2001).

Muller et al., "Vascular Endothelial Growth Factor: Crystal Structure and Functional Mapping of the Kinase Domain Receptor Binding Site," Proc. Natl. Acad. Sci. USA 94: 7192-7197 (1997).

Mutter et al., "Molecular Mechanisms for Preeclampsia," Microvasc. Res. 75(1): 1-12 (2008).

Myers et al., "Hypertensive Diseases and Eclampsia," Curr. Opin. Obstet. Gynecol. 14: 119-125 (2002).

Neufeld et al., "Similarities and Differences Between the Vascular Endothelial Growth Factor (VEGF) Splice Variants," Cancer Metastasis 15: 153-158 (1996).

Newman et al., "Cigarette Smoking and Pre-Eclampsia: Their Association and Effects on Clinical Outcomes," J Matern. Fetal. Med. 10: 166-170 (2001).

Ong et al., "First-Trimester Maternal Serum Levels of Placental Growth Factor as Predictor of Preeclampsia and Fetal Growth Restriction," Obstet. Gynecol. 98: 608-611 (2001).

Ostendorf et al., "VEGF (165) Mediates Glomerular Endothelial Repair," J. Clin. Invest. 104: 913-923 (1999).

Page et al., "Excessive Placental Secretion of Neurokinin B During the Third Trimester Causes Pre-Eclampsia," Nature 405: 797-800 (2000).

Parikh et al., "Putting Pressure on Pre-Eclampsia," Nat. Med. 14(8): 810-812 (2008).

Park et al., "Placenta Growth Factor Potentiation of Vascular Endothelial Growth Factor Bioactivity, in Vitro and in Vivo, and High Affinity Binding to Flt-1 but not to Flk-1/KDR," J. Biol. Chem. 269: 25646-25654 (1994).

Park et al., "An Elevated Maternal Plasma, but not Amniotic Fluid, Soluble fms-Like Tyrosine Kinase-1 (sFlt-1) at the Time of Mid-trimester Genetic Amniocentesis is a Risk Factor for Preeclampsia," Am. J. Obstet. Gynecol. 193: 984-989 (2005).

Paternoster et al., "Markers of Tubular Damage in Pre-Eclampsia," Minerva Ginecol. 51: 373-377 (1999).

Polliotti et al., "Second-Trimester Maternal Serum Placental Growth Factor and Vascular Endothelial Growth Factor for Predicting Severe, Early-Onset Pre-Eclampsia," Obstet. Gynecol. 101: 1266-1274 (2003).

Powers et al., "Maternal Serum Soluble fms-like Tyrosine Kinase 1 Concentrations are not Increased in Early Pregnancy and Decrease More Slowly Postpartum in Women Who Develop Preeclampsia," Am. J. Obstet. Gynecol. 193: 185-191 (2005).

Qazi et al., "Soluble Fms-like Tyrosine Kinase Associated with Preeclampsia in Pregnancy in Systemic Lupus Erythematosus," J. Rheumatol. 35: 1-4 (2008).

Rajakumar et al., "Extra-Placental Expression of Vascular Endothelial Growth Factor Receptor-1, (Flt-1) and Soluble Flt-1 (Sflt-1), by Peripheral Blood Mononuclear Cells (Pbmcs) in Normotensive and Preeclamptic Pregnant Women," Placenta 26(7): 563-573 (2004).

Rana et al., "Sequential Changes in Antiagiogenic Factors in Early Pregnancy and Risk of Developing Preeclampsia," Hypertension 50(1): 137-142 (2007).

Regnault et al., "Placental Expression of VEGF, PlGF and Their Receptors in a Model of Placental Insufficiency—Intrauterine Growth Restriction (PI-IUGR)," Placenta 23: 132-144 (2002).

Reuvekamp et al., "Selective Deficit of Angiogenic Growth Factors Characterizes Pregnancies Complicated by Pre-eclampsia," BJOG 106: 1019-1022 (1999).

Roberts et al., "Pathogenesis and Genetics of Pre-Eclampsia," Lancet 357: 53-56 (2001).

Roes et al., "High Levels of Urinary Vascular Endothelial Growth Factor in Women with Severe Preeclampsia," Int. J. Biol. Markers 19: 72-75 (2004).

Romero et al., "A Longitudinal Study of Angiogenic (Placental Growth Factor) and Anti-Angiogenic (Soluble Endoglin and Soluble Vascular Endothelial Growth Factor Receptor-1) Factors in Normal Pregnancy and Patients Destined to Develop Preeclampsia and Deliver a Small for Gestational Age Neonate," J. Matern. Fetal Neonatal Med. 21(1): 9-23 (2008).

Salahuddin et al., "Diagnostic Utility of Soluble Fms-Like Tyrosine Kinase 1 and Soluble Endoglin in Hypertensive Diseases of Pregnancy," Am. J. Obstet. Gynecol. 197(1): 28.e1-6 (2007).

Shan et al., "Use of Circulating Antiangiogenic Factors to Differentiate Other Hypertensive Disorders From Preeclampsia in a Pregnant Woman on Dialysis," Am. J. Kidney Dis. 51(6): 1029-1032 (2008).

Sibai, "Diagnosis and Management of Gestational Hypertension and Preeclampsia," Obstet. Gynecol. 102: 181-192 (2003).

Sibai et al., "What We Have Learned About Preeclampsia," Semin. Perinatol. 27: 239-246 (2003).

Signore et al., "Circulating Soluble Endoglin and Placental Abruption," Prenat. Diagn. 28(9): 852-858 (2008).

Steinberg et al., "Angiogenic Factors and Preeclampsia," Thromb Res. 123 Suppl. 2: S93-99 (2009).

Stillman et al., "The Glomerular Injury of Preeclampsia," J. Am. Soc. Nephrol. 18(8): 2281-2284 (2007).

Strevens et al., "Glomerular Endotheliosis in Normal Pregnancy and Pre-Eclampsia," Br. J. Obstet. Gynaecol. 10: 831-836 (2003).

Su et al., "Decreased Maternal Serum Placenta Growth Factor in Early Second Trimester and Pre-Eclampsia," Obstet. Gynecol. 97: 898-904 (2001).

Sugimoto et al., "Neutralization of Circulating Vascular Endothelial Growth Factor (VEGF) by Anti-VEGF Antibodies and Soluble VEGF Receptor 1 (sFlt-1) Induces Proteinuria," J. Biol. Chem. 278: 12605-12608 (2003).

Taylor et al., "Longitudinal Serum Concentrations of Placental Growth Factor: Evidence for Abnormal Placental Angiogenesis in Pathologic Pregnancies," Am. J. Obstet. Gynecol. 188: 177-182 (2003).

Thadhani et al., "First Trimester Placental Growth Factor and Soluble Fms-Like Tyrosine Kinase 1 and Risk for Preeclampsia," J. Clin. Endocrinol. Metab. 89: 770-775 (2004).

Thadhani et al., "Hypertension During Pregnancy: A Disorder Begging for Pathophysiological Support," Hypertension 46(6): 1250-1251 (2005).

Thatcher et al., "Pregnancy induced hypertension: development of a model in the pregnant sheep," Am. J. Obstet. Gynecol. 155: 201-207 (1986).

Tidwell et al., "Low Maternal Serum Levels of Placenta Growth Factor as an Antecedent of Clinical Pre-Eclampsia," Am. J. Obstet. Gynecol. 184: 1267-1272 (2001).

Tischer et al., "The Human Gene for Vascular Endothelial Growth Factor," J. Biol. Chem. 266: 11947-11954 (1991).

Tjoa et al., "Plasma Placenta Growth Factor Levels in Midtrimester Pregnancies," Obstet. Gynecol. 98: 600-607 (2001).

Tjoa et al., "Angiogenic Factors and Preeclampsia," Front Biosci. 12: 2395-2402 (2007).

Torry et al., "Preeclampsia is Associated with Reduced Serum Levels of Placenta Growth Factor," Am. J. Obstet. Gynecol. 179: 1539-1544 (1998).

Tsatsaris et al., "Overexpression of the Soluble Vascular Endothelial Growth Factor Receptor in Preeclamptic Patients: Pathophysiological Consequences," J Clin. Endocrinol. Metab. 88: 5555-5563 (2003).

Tucci et al., "rhVEGF and Experimental Rat Skin Flaps: Systemic or Local Administration and Morphological Characteristics," 24: 743-751 (2001).

Vuorela, et al., "Amniotic Fluid-Soluble Vascular Endothelial Growth Factor Receptor-1 in Preeclampsia," Obstet. Gynecol. 95: 353-357 (2000).

Walker, "Pre-eclampsia," Lancet 356: 1260-1265 (2000).

Walsh et al., "Computer Modeling of the Receptor-Binding Domains of VEGF and PIGF," Protein Eng. 10: 389-398 (1997).
Wang et al., "Preeclampsia: The Role of Angiogenic Factors in Its Pathogenesis," Physiology 24: 147-158 (2009).
Widmer et al., "Mapping the Theories of Preeclampsia and The Role of Angiogenic Factors: A Systematic Review," Obstet. Gynecol. 109(1): 168-180 (2007).
Wiesmann et al., "Crystal Structure at 1.7 Å Resolution of VEGF in Complex with Domain 2 of the Flt-1 Receptor," Cell 91: 695-704 (1997).
Wolf et al., "Circulating Levels of the Antiangiogenic Marker Sflt-1 are Increased in First Versus Second Pregnancies," Am. J. Obstet. Gynecol. 193(1): 16-22 (2005).
Zhou et al., "Preeclampsia is Associated with Failure of Human Cytotrophoblasts to Mimic a Vascular Adhesion Phenotype. One Cause of Defective Endovascular Invasion in This Syndrome?," J. Clin. Invest 99: 2152-64 (1997).
Zhou et al., "Vascular Endothelial Growth Factor Ligands and Receptors That Regulate Human Cytotrophoblast Survival are Dysregulated in Severe Preeclampsia and Hemolysis, Elevated Liver Enzymes, and Low Platelets Syndrome," Am. J. Pathol. 160: 1405-1423 (2002).
Baek et al., Hypoxia-Induced VEGF Enhances Tumor Survivability via Suppression of Serum Deprivation-Induced Apoptosis. Oncogene 19:4621-4631 (2000).
Baker et al., "Elevated Serum Levels of Vascular Endothelial Growth Factor in Patients with Preeclampsia," Obstet. Gynocol. 86: 815-821 (1995).
Baumgartner et al., "Constitutive Expression of ph VEGF165 After Intramuscular Gene Transfer Promotes Collateral Vessel Development in Patients with Critical Limb Ischemia," Circulation 97:1114-1123 (1998).
Belgore et al., "Plasma Levels of Vascular Endothelial Growth Factor and its Soluble Receptor (SFlt-1) in Essential Hypertension," Am. J. Cardiol. 87:805-807 (2001).
Blann et al., "Plasma Vascular Endothelial Growth Factor and its Receptor Flt-1 in Patients with Hyperlipidemia and Atherosclerosis and the Effects of Fluvastatin or Fenofibrate," Am. J. Cardiol. 87: 1160-1163 (2001).
Bouletreau et al., "Hypoxia and VEGF Up-Regulate BMP-2 mRNA and Protein Expression in Microvascular Endothelial Cells: Implications for Fracture Healing," Plast. Reconstr. Surg. 109: 2384-2397 (2002).
Charnock-Jones et al., "Determination of the Circulating Levels of the Soluble Form of the VEGF-R1 (sFlt-1) in Women at High Risk of Developing Pre-Eclampsia." J. Soc. Gynecol. Investig.10: 230 (2003).
Cohen et al., "Amelioration of Diabetic Nephropathy by Treatment with Monoclonal Antibodies Against Glycated Albumin," Kidney International 45: 1673-1679 (1994).
Davis-Smyth et al., "Mapping the Charged Residues in the Second Immunoglobulin-Like Domain of the Vascular Endothelial Growth Factor/Placenta Growth Factor Receptor Flt-1 Required for Binding and Structural Stability," J. Biol. Chem. 273: 3216-3222 (1998).
Davison et al., "New Aspects in the Pathophysiology of Preeclampsia," J. Am. Soc. Nephrol. 15: 2440-2448 (2004).
Del-Sorbo et al., "The Synthesis of Platelet-Activating Factor Modulates Chemotaxis of Monocytes Induced by HIV-1 Tat," Eur. J. Immunol. 29: 1513-1521 (1999).
Deodato et al., "Recombinant AAV Vector Encoding Human VEGF165 Enhances Wound Healing," Gene Therapy 9: 777-785 (2002).
Dvorak, "Vascular Permeability Factor/Vascular Endothelial Growth Factor: A Critical Cytokine in Tumor Angiogenesis and a Potential Target for Diagnosis and Therapy," J. Clin. Oncol. 20: 4368-4380 (2002).
Eddahibi et al., "Imbalance Between Platelet Vascular Endothelial Growth Factor and Platelet-Derived Growth Factor in Pulmonary Hypertension," Am. J. Respir. Crit. Care Med. 162: 1493-1499 (2000).
Errico et al., "Identification of Placenta Growth Factor Determinants for Binding and Activation of Flt-1 Receptor," J. Biol. Chem. 279: 43929-43939 (2004).

Freedman et al., "Therapeutic Angiogenesis for Coronary Artery Disease," Ann. Intern. Med. 136: 54-71 (2002).
Gordon et al., "Phase I Safety and Pharmacokinetic Study of Recombinant Human Anti-Vascular Endothelial Growth Factor in Patients with Advanced Cancer," J. Clin. Oncol. 19: 843-850 (2001).
Graubert et al., "Vascular Repair After Menstruation Involves Regulation of Vascular Endothelial Growth Factor-Receptor Phosphorylation by sFLT-1," Am. J. Pathol. 158: 1399-1410 (2001).
Henry et al., "Intracoronary Administration of Recombinant Human Vascular Endothelial Growth Factor to Patients with Coronary Artery Disease," Am. Heart J. 142: 872-880 (2001).
Holzgreve et al., "Disturbed Feto-Maternal Cell Traffic in Preeclampsia," Obstet. Gynecol. 91: 669-672 (1998).
Isner et al., "VEGF Gene Transfer for Diabetic Neuropathy," Human Gene Ther. 12: 1593-1594 (2001).
Isner, "Myocardial Gene Therapy," Nature 415: 234-239 (2002).
Kaku et al., "Effects of Vascular Endothelial Growth Factor on Osteoclast Induction During Tooth Movement in Mice," J. Dent. Res. 80:1880-1883 (2001).
Kincaid-Smith, "The Renal Lesion of Preeclampsia Revisited," Am. J. Kidney Dis. 17: 144-148 (1991).
Knebelmann et al., "Transforming Growth Factor as Alpha Is a Target for the Von Hippel-Lindau Tumor Suppressor," Cancer Res. 58: 226-231 (1998).
Koransky, "VEGF Gene Delivery for Treatment of Ischemic Cardiovascular Disease," Trends Cardiovasc. Med. 12: 108-114 (2002).
Krussel et al., "Expression of mRNA for Vascular Endothelial Growth Factor Transmembraneous Receptors Flt1 and KDR, and the Soluble Receptor sflt in Cycling Human Endometrium," Mol. Hum. Reprod. 5: 452-458 (1999).
Kuo et al., "Comparative Evaluation of the Antitumor Activity of Antiangiogenic Proteins Delivered by Gene Transfer," Proc. Natl. Acad. Sci. U S A 98: 4605-4610 (2001).
Lai et al., "Inhibition of Angiogenesis by Adenovirus-Mediated sFlt-1 Expression in a Rat Model of Corneal Neovascularization," Hum. Gene Ther. 12: 1299-1310 (2001).
Lai et al., "Potential Long-Term Inhibition of Ocular Neovascularisation by Recombinant Adeno-Associated Virus-Mediated Secretion Gene Therapy," Gene Ther. 9: 804-813 (2002).
Lecouter et al., "Identification of an Angiogenic Mitogen Selective for Endocrine Gland Endothelium," Nature 412: 868-869 (2001).
Levine et al., "Circulating Angiogenic Factors and the Risk of Preeclampsia," N. Engl. J. Med. 350: 672-683 (2004).
Levine et al., "Urinary Placental Growth Factor and Risk of Preeclampsia," JAMA 293: 77-85 (2005).
Lip et al., "Plasma VEGF and Soluble VEGF Receptor FLT-1 in Proliferative Retinopathy: Relationship to Endothelial Dysfunction and Laser Treatment," Invest. Ophthalmol. Vis. Sci. 41: 2115-2119 (2000).
Moran et al., "Glomerular Ultrafiltration in Normal and Preeclamptic Pregnancy," J. Am. Soc. Nephrol. 14: 648-652 (2003).
Muller et al., "The Crystal Structure of Vascular Endothelial Growth Factor (VEGF) Refined to 1.93 Å Resolution: Multiple Copy Flexibility and Receptor Binding," Structure 5: 1325-1338 (1997).
Nishimoto et al., "Glomerular Hypertrophy in Preeclamptic Patients with Focal Segmental Glomerulosclerosis: A Morphometric Analysis," Clin. Nephrol. 51: 209-219 (1999).
Olofsson et al., "Vascular Endothelial Growth Factor B (VEGF-B) Binds to VEGF Receptor-1 and Regulates Plasminogen Activator Activity in Endothelial Cells," Proc. Natl. Acad. Sci. USA 95: 11709-11714 (1998).
Parry et al., "Dinucleotide Repeat Polymorphisms Within the Flt-1 Gene in Minimal Change Nephropathy," Eur. J. Immunogenet. 26: 321-323 (1999).
Quirici et al., "Differentiation and Expansion of Endothelial Cells From Human Bone Marrow CD 133+ Cells," Br. J. Haematol. 115: 186-194 (2001).
Roberts, "Endothelial Dysfunction in Preeclampsia," Semin. Reprod. Endocrinol. 16: 5-15 (1998).
Sato et al., "Increased Pulmonary Vascular Contraction to Serotonin after Cardiopulmonary Bypass: Role of Cyclooxygenase," J. Surg. Res. 90: 138-143 (2000).

Sawano et al., "Flt-1 but not KDR/Flk-1 Tyrosine Kinase is a Receptor for Placenta Growth Factor, Which is Related to Vascular Endothelial Growth Factor," Cell Growth Differ. 7: 213-221 (1996).

Simon et al., "Expression of Vascular Endothelial Growth Factor and Its Receptors in Human Renal Ontogenesis and in Adult Kidney," Am. J. Physiol. 268: F240-F250 (1995).

Torry et al., "Expression and Function of Placenta Growth Factor: Implications for Abnormal Placentation," J. Soc. Gynecol. Investig.. 10: 178-188 (2003).

Traver et al., "Walking the Walk: Migration and Other Common Themes in Blood and Vascular Development," Cell 108: 731-734 (2002).

Vuorela, "Vascular Endothelial Growth Factor, Its Receptors, and the Tie Receptor in Normal and Complicated Pregnancy," Department of Obstetrics and Gynecology, Helsinki University Central Hospital, University of Helsinki, Finland (2000).

Yang et al., "sFlt-1 Gene-Transfected Fibroblasts: A Wound-Specific Gene Therapy Inhibits Local Cancer Recurrence," Cancer Res. 61: 7840-7845 (2001).

Yang et al., "A Randomized Trial of Bevacizumab, an Anti-Vascular Endothelial Growth Factor Antibody, for Metastatic Renal Cancer," N. Engl. J. Med. 349: 427-434 (2003).

Zhang et al., "Birth-Weight-for-Gestational-Age-Patterns by Race, Sex, and Parity in the United States Population," Obstet. Gynecol. 86: 200-208 (1995).

Redman, C.W. et al., "Latest advances in understanding preeclampsia." Science 308:1592-1594 (2005).

Sugimoto, H. et al., "Neutralization of circulating vascular endothelial growth factor (VEGF) by anti-VEGF antibodies and soluble VEGF receptor 1 (sFlt-1) induces proteinuria," J. Biol. Chem. 278:12605-12608 (2003).

Takanashi, K. et al., "Detection and measurement of urinary 2-hydroxyestradiol 17-sulfate a potential placental antioxidant during pregnancy," Clin. Chem. 46(3):373-378 (2000).

Tempfer, C. et al. "Applications of polymorphisms and pharmacogenomics in obstetrics and gynecology," Pharmacogenomics, Ashley Publications, GB, 5(1):57-65 (2004).

Vuorela, P. et al., "Amniotic fluid-soluble vascular endothelial growth factor receptor-1 in preeclampsia," Obstet. Gynecol. 95:353-357 (2000).

Wonodi, I. et al., "Association Between Val 108/158 Met Polymorphism of the COMT Gene and Schizophrenia," Am. J. Med. Genet. 120B:47-50 (2003).

Xie et al., "Characterization and Implications of Estrogenic Down-Regulation of Human Catechol-O-Methyltransferase Gene Transcription," Molecular Pharmacology 56(31):31-38 (1999).

Koos, B., Management of Uncorrected, Palliated, and Repaired Cyanotic Congenital Heart Disease in Pregnancy, Progress in Pediatric Cardiology pp. 25-45 (2004).

Mordel, N. et al., Successful Full-Term Pregnancy in Familial Mediterranean Fever Complicated with Amyloidosis, Fetal Diagn Ther. pp. 129-134 (1993).

Kono, S., et al. "Radioimmunoassay and Metabolic Clearance Rate of Catecholestrogens, 2-Hydroxyestrone and 2-Hydroxyestradiol in Man" J. Steroid Biochem., vol. 19, No. 1, 1983 pp. 627-633.

Park J., et al., "Hypoxia-Inducible Factor 1-Related Diseased and Prospective Therapeutic Tools" J. Pharmacol Sci 94, 2004, pp. 221-232.

Sun, et al., "Association between catechol-methyltransferase gene polymorphism and pregnanc induced hypertension" Database Medline [Online] US National Library of Medicine (NLM), Bethesda, MD, US, Accession No. NLM14989982, Abstract. XP-002568262, Jan. 1, 2004.

\* cited by examiner

METHODS AND COMPOSITIONS FOR TREATMENT OF PREECLAMPSIA

BACKGROUND

Preeclampsia is a hypertensive, multi-system disorder of pregnant women that affects approximately 6% of first pregnancies and 1-2% of all pregnancies (MacGillivary, I., Preeclampsia: the hypertensive disease of pregnancy. W.B. Saunders, Philadelphia 1987:17). Preeclampsia is a major cause of maternal and fetal mortality and morbidity, and is a disease unique to human beings during pregnancy. Hospitalization, strict bed rest, magnesium sulfate administration to prevent convulsions, and prompt delivery remain the current standard of therapy for preeclampsia. Complications of preeclampsia include eclamptic seizures, hemolysis, elevated liver function tests, low platelet count (HELLP) syndrome, hepatic rupture, DIC pulmonary edema, acute renal failure, placental abruption, intrauterine fetal demise (IUFD), cerebral hemorrhage, cortical blindness, and retinal detachment. Despite many years of study, the causes of preeclampsia are unclear.

The hallmarks of preeclampsia include hypertension, proteinuria, and edema. Underlying these clinical manifestations, placental maladaptation and body-wide endothelial cell dysfunction occur (Khong, T. Y. et al. (1986) Br. J. Obstet. Gynecol. 93:1049-1059; Roberts, J. M. et al. (1991) Am. J. Hypertens. 4:700-708). Failure of trophoblastic invasion into myometrial segments of maternal spiral arteries and the production of cytotoxic mediators which cause systemic endothelial damage also seem to be implicated.

During normal development human trophoblasts invade through the extracellular matrix into the myometrial portion of spiral arteries and convert them into uteroplacental arteries (Pijnenborg et al., in Trophoblast Research (Denker and Aplin, eds.) Plenum Press, New York, p. 333 (1990)). Uteroplacental arteries then dilate approximately 30-fold as large as the spiral arteries. Resulting hemodynamic changes enable the placental bed to satisfy the increased demand for oxygen from the fetus during the latter stages of gestation. In preeclamptic women, however, spiral arteries are not properly converted into uteroplacental arteries due to the failure of the second wave of trophoblastic migration into the myometrium at the beginning of the second trimester (Khong et al. (1986) Br. J. Obstet. Gynecol. 93:1049-1059). As a result, preeclamptic women typically demonstrate a high-resistance, high-pressure, and low-flow state with intact, non-dilated spiral arteries (Robertson et al. (1986) Am. J. Obstet. Gynecol. 155:401-412), and demonstrate a wide variety of clinical syndromes.

Preeclampsia may be divided into mild and severe forms. Mild preeclampsia is indicated where the patient exhibits hypertension, a proteinuria level of greater than 300 mg per 24 hour period, mild edema signaled by weight gain of greater than 2 pounds per week or 6 pounds per month, and urine output of less than 500 ml per 24 hour period. Severe preeclampsia is indicated where the patient's blood pressure is greater than 160/110 on two occasions at least six hours apart while on bed rest or a systolic blood pressure increase of greater than 60 over a baseline value or a diastolic increase of greater than 30. In addition, a proteinuria level of greater than 5 g per 24 hour period or a reading of 31 or 41 on a urine dipstick, massive edema, oliguria (less than 400 ml per 24 hour period), presence of fetal growth retardation (IUGR), or systemic symptoms including pulmonary edema, headaches, visual changes, right upper quadrant pain, elevated liver enzymes or thrombocytopenia.

After a diagnosis of preeclampsia, the baby is generally induced and delivered if it is near term, i.e., after 36 weeks. However, if preeclampsia occurs earlier in the pregnancy, its impact is more profound. The only "cure" for the disease is delivery of the baby, which is generally contrary to the best interests of the baby if it is not near term. However, if the condition does not respond to traditional management options, early delivery may be the only option remaining. Traditional management includes bed rest, antihypertensive therapy, including methyldopa (Aldomet™), atenolol, and labetalol. If the term of pregnancy from the diagnosis of preeclampsia to delivery could be extended safely for both the fetus and mother, then significant improvement in perinatal outcomes may be achieved.

It is therefore an object of the present invention to overcome these shortcomings in existing treatments for preeclampsia by providing safe and effective methods and compositions for the treatment of preeclampsia and other pregnancy related disorders.

SUMMARY

Featured herein are novel diagnostic and therapeutic methods that will permit safer and more effective treatment of preeclampsia. In one aspect, a method for treating or preventing preeclampsia is provided, wherein the method comprises administering to a pregnant subject in need thereof an effective amount of 2-methoxyestradiol (2-ME), an analog thereof, or a pharmaceutically acceptable salt or prodrug thereof. In various embodiments, the method further comprises determining the level of 2-methoxyestradiol and/or an analog thereof in a biological subject from a subject. In an exemplary embodiment, the biological sample is urine, blood, or plasma.

In a second aspect, a method for diagnosing, or predicting the development of, preeclampsia in a subject is provided, wherein the method comprises determining the level of 2-methoxyestradiol, a 2-methoxyestradiol metabolite, or a 2-methoxyestradiol precursor in a biological sample from said subject and comparing said level to the level of 2-methoxyestradiol, a 2-methoxyestradiol metabolite, or a 2-methoxyestradiol precursor in a control, wherein said control is a predetermined standard from at least one non-preeclamptic subject at about the same stage of pregnancy as said subject, and wherein a lower level of 2-methoxyestradiol, a 2-methoxyestradiol metabolite, or a 2-methoxyestradiol precursor in said subject sample as compared to the control is indicative of a subject susceptible to, or suffering from, preeclampsia. In an exemplary embodiment, the biological sample is urine, blood or plasma.

DETAILED DESCRIPTION

Definitions

Figure 1:
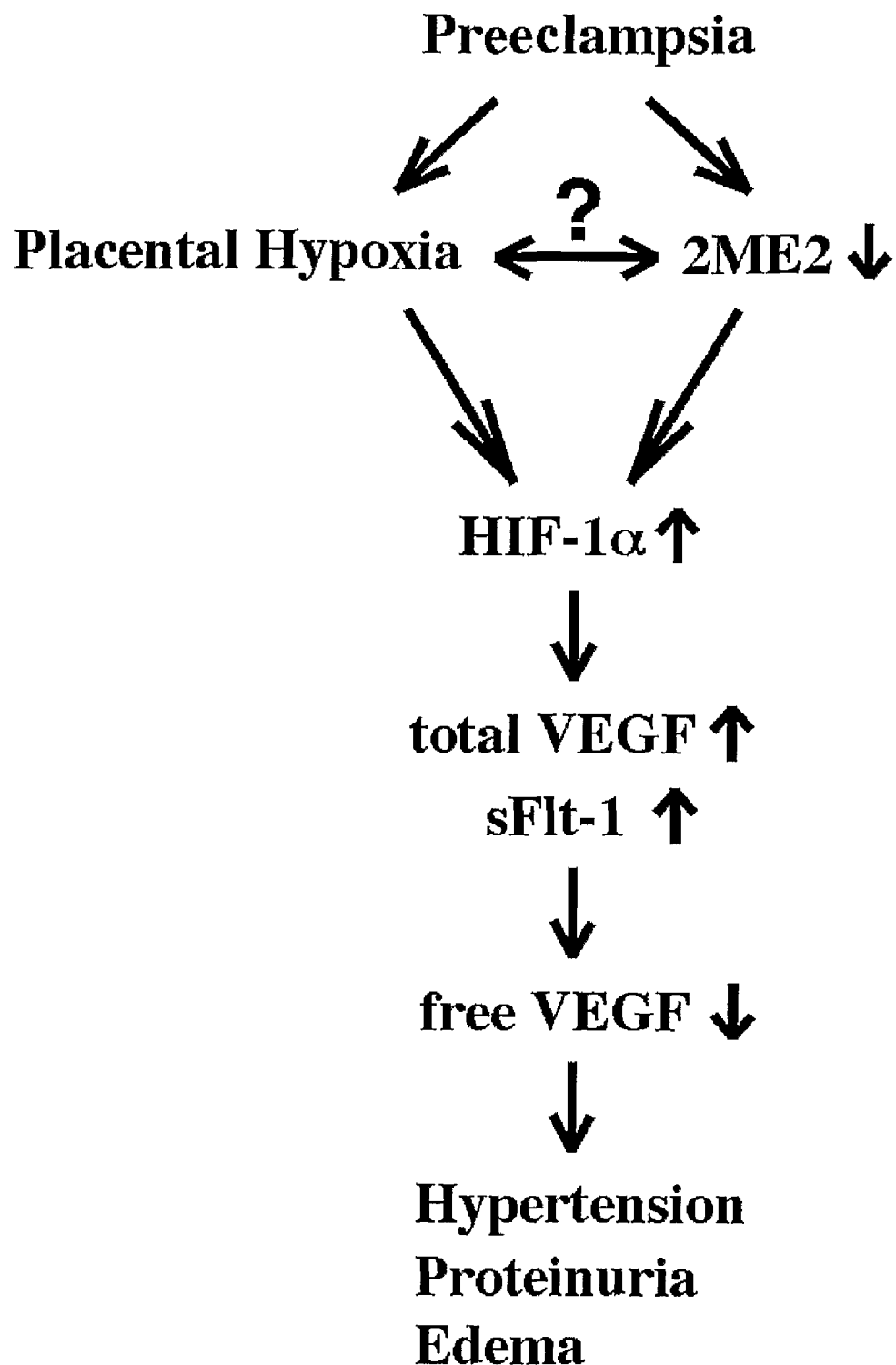
FIG. 1 is a diagram showing the interaction of 2-methoxyestrodial, HIF-1α, VEGF, and sFlt-1 in preeclampsia.

For convenience, certain terms employed in the specification, examples, and appended claims are collected here. Unless defined otherwise, all technical and scientific terms used herein have the same meaning as commonly understood by one of ordinary skill in the art to which this invention belongs.

The articles "a" and "an" are used herein to refer to one or to more than one (i.e., to at least one) of the grammatical object of the article. By way of example, "an element" means one element or more than one element.

The terms "comprise" and "comprising" are used in the inclusive, open sense, meaning that additional elements may be included.

The term "including" is used to mean "including but not limited to". "Including" and "including but not limited to" are used interchangeably.

The term "control", as used herein with reference to the level of 2-methoxyestradiol (or a precursor or metabolite thereof), refers to the level of 2-methoxyestradiol (or a precursor or metabolite thereof) in at least one subject not suffering from a given "pregnancy disorder". The control may reflect the average or mean value of the level of 2-methoxyestradiol (or a precursor or metabolite thereof) from two or more subjects not suffering from a given "pregnancy disorder". The control value may be from one or more subjects at approximately the same stage of pregnancy as the test subject being compared to the control. Subjects at the "same stage of pregnancy" is meant to encompass pregnant subjects in approximately the same month of pregnancy, approximately the same week of pregnancy, or approximately the same day of pregnancy. In an exemplary embodiment, subjects at the "same stage of pregnancy" refers to subjects at approximately the same week of pregnancy. The control may be a predetermined level of 2-methoxyestradiol (or a precursor or metabolite thereof) at one or more stages of pregnancy. In one embodiment, the control is a graph or chart representing control levels of 2-methoxyestradiol (or a precursor or metabolite thereof) at a variety of stages of pregnancy. In an exemplary embodiment, the control is a graph or chart representing control levels of 2-methoxyestradiol (or a precursor or metabolite thereof) throughout all stages of pregnancy (e.g., on a trimester by trimester, month by month, week by week, or day by day basis).

The term "pregnancy disorder", as used herein, refers to any disease or disorder of pregnancy that is associated with an abnormal level of 2-methoxyestradiol in a subject. Diseases or disorders "associated with an abnormal level of 2-methoxyestradiol" is meant to encompass diseases or disorders that are directly or indirectly caused by an abnormal level of 2-methoxyestradiol or diseases or disorders having an independent underlying cause but that are associated with an abnormal level of 2-methoxyestradiol in a subject. A pregnancy disorder may refer to a disease or disorder of pregnancy wherein a subject has a higher level of 2-methoxyestradiol than a control subject. Alternatively, a pregnancy disorder may refer to a disease or disorder of pregnancy wherein a subject has a lower level of 2-methoxyestradiol than a control subject. A pregnancy disorder may refer to a disease or disorder of pregnancy associated with abnormal angiogenesis of the mother, fetus, placenta, uterus, etc. Additionally, a pregnancy disorder may refer to a post pregnancy disorder that is related to, or caused by, the prior pregnancy. Examples of pregnancy disorders include one or more of the following: preeclampsia, eclampsia, hypertension, edema, IUGR (Intrauterine Growth Retardation), HELPP syndrome (Hemolysis, Elevated Liver Enzymes, and Low Platelet count), placental separation, placenta previa, ectopic pregnancy, or retained placenta. In an exemplary embodiment, a pregnancy disorder refers to preeclampsia.

The term "2-methoxyestradiol analog" refers to a derivative or analog of 2-methoxyestradiol that exhibits a therapeutic effect similar to that of 2-methoxyestradiol when administered to a subject suffering from a "pregnancy disorder". In an exemplary embodiment, a 2-methoxyestradiol analog exhibits a therapeutic effect when administered to a subject suffering from preeclampsia. In one embodiment, a 2-methoxyestradiol analog exhibits greater stability when administered to a subject than 2-methoxyestradiol itself. In an exemplary embodiment, a 2-methoxyestradiol analog is a compound of Formula I. Examples of 2-methoxyestradiol analogs suitable for use in association with the methods described herein are also described in various U.S. patents and published applications, including, for example, U.S. Pat. No. 6,528,676, and U.S. Patent Application Publication Nos. 2003/0236408, 2002/0147183, 2003/0187076, and 2003/0236439. In an exemplary embodiment, analogs of 2-methoxyestradiol include colchicine and combretastatin A-4.

The term "precursor", as used herein with reference to 2-methoxyestradiol, or a 2-methoxyestradiol analog, refers to a compound that forms 2-methoxyestradiol, or a 2-methoxyestradiol analog, as at least one of the metabolites formed during a metabolic process. In an exemplary embodiment, precursors of 2-methoxyestradiol include, for example, estradiol, 2-hydroxyestradiol, etc.

The term "metabolite", as used herein with reference to 2-methoxyestradiol, or a 2-methoxyestradiol analog, refers to a compound that is formed by metabolism of 2-methoxyestradiol, or a 2-methoxyestradiol analog. Metabolite is meant to encompass both anabolites and catabolites. In an exemplary embodiment, metabolites of 2-methoxyestradiol include, for example, 2-methoxyestrone, etc.

The term "biological sample" refers to a sample of biological material obtained from a subject, or present within a subject, including a tissue, tissue sample, or cell sample (e.g., a chorionic villus sample or a tissue biopsy, for example, an aspiration biopsy, a brush biopsy, a surface biopsy, a needle biopsy, a punch biopsy, an excision biopsy, an open biopsy, an incision biopsy, or an endoscopic biopsy), tumor, tumor sample, or biological fluid (e.g., blood, serum, plasma, amniotic fluid, urine, lymph, or spinal fluid). In an exemplary embodiment, a subject may be a human subject.

The term "about a control level", as used herein with reference to the level of 2-methoxyestradiol and/or an analog thereof in a subject, refers to a level of 2-methoxyestradiol that is less than 50%, 30%, 25%, 20%, 15%, 10%, 5%, 2%, or 1% different from the control level of 2-methoxyestradiol.

The term "cis" is art-recognized and refers to the arrangement of two atoms or groups around a double bond such that the atoms or groups are on the same side of the double bond. Cis configurations are often labeled as (Z) configurations.

The term "trans" is art-recognized and refers to the arrangement of two atoms or groups around a double bond such that the atoms or groups are on the opposite sides of a double bond. Trans configurations are often labeled as (E) configurations.

The term "covalent bond" is art-recognized and refers to a bond between two atoms where electrons are attracted electrostatically to both nuclei of the two atoms, and the net effect of increased electron density between the nuclei counterbalances the internuclear repulsion. The term covalent bond includes coordinate bonds when the bond is with a metal ion.

The term "therapeutic agent" is art-recognized and refers to any chemical moiety that is a biologically, physiologically, or pharmacologically active substance that acts locally or systemically in a subject. Examples of therapeutic agents, also referred to as "drugs", are described in well-known literature references such as the Merck Index, the Physicians Desk Reference, and The Pharmacological Basis of Therapeutics, and they include, without limitation, medicaments; vitamins; mineral supplements; substances used for the treatment, prevention, diagnosis, cure or mitigation of a disease or illness; substances which affect the structure or function of the body; or pro-drugs, which become biologically active or more active after they have been placed in a physiological environment.

The term "therapeutic effect" is art-recognized and refers to a local or systemic effect in animals, particularly mammals, and more particularly humans caused by a pharmacologically active substance. The term "pharmacologically active substance" includes any substance intended for use in the diagnosis, cure, mitigation, treatment or prevention of disease or in the enhancement of desirable physical or mental development and/or conditions in an animal or human. The phrase "therapeutically-effective amount" means that amount of such a substance that produces some desired local or systemic effect at a reasonable benefit/risk ratio applicable to any treatment. The therapeutically effective amount of such substance will vary depending upon the subject and disease condition being treated, the weight and age of the subject, the severity of the disease condition, the manner of administration and the like, which can readily be determined by one of ordinary skill in the art. For example, certain compositions described herein may be administered in a sufficient amount to produce a at a reasonable benefit/risk ratio applicable to such treatment.

The term "synthetic" is art-recognized and refers to production by in vitro chemical or enzymatic synthesis.

The term "meso compound" is art-recognized and refers to a chemical compound which has at least two chiral centers but is achiral due to a plane or point of symmetry.

The term "chiral" is art-recognized and refers to molecules which have the property of non-superimposability of the mirror image partner, while the term "achiral" refers to molecules which are superimposable on their mirror image partner. A "prochiral molecule" is a molecule which has the potential to be converted to a chiral molecule in a particular process.

The term "stereoisomers" is art-recognized and refers to compounds which have identical chemical constitution, but differ with regard to the arrangement of the atoms or groups in space. In particular, "enantiomers" refer to two stereoisomers of a compound which are non-superimposable mirror images of one another. "Diastereomers", on the other hand, refers to stereoisomers with two or more centers of dissymmetry and whose molecules are not mirror images of one another.

Furthermore, a "stereoselective process" is one which produces a particular stereoisomer of a reaction product in preference to other possible stereoisomers of that product. An "enantioselective process" is one which favors production of one of the two possible enantiomers of a reaction product.

The term "regioisomers" is art-recognized and refers to compounds which have the same molecular formula but differ in the connectivity of the atoms. Accordingly, a "regioselective process" is one which favors the production of a particular regioisomer over others, e.g., the reaction produces a statistically significant increase in the yield of a certain regioisomer.

The term "epimers" is art-recognized and refers to molecules with identical chemical constitution and containing more than one stereocenter, but which differ in configuration at only one of these stereocenters.

The term "$ED_{50}$" is art-recognized. In certain embodiments, $ED_{50}$ means the dose of a drug which produces 50% of its maximum response or effect, or alternatively, the dose which produces a pre-determined response in 50% of test subjects or preparations. The term "$LD_{50}$" is art-recognized. In certain embodiments, $LD_{50}$ means the dose of a drug which is lethal in 50% of test subjects. The term "therapeutic index" is an art-recognized term which refers to the therapeutic index of a drug, defined as $LD_{50}/ED_{50}$.

The term "prodrug" is art-recognized and is intended to encompass compounds which, under physiological conditions, are converted into a drug, such as, for example, a 2-methoxyestradiol compound as described herein. A common method for making a prodrug is to select and attach moieties which are hydrolyzed under physiological conditions to provide the desired compound. In other embodiments, the prodrug is converted by an enzymatic activity of the host animal.

The term "structure-activity relationship" or "(SAR)" is art-recognized and refers to the way in which altering the molecular structure of a drug or other compound alters its interaction with a receptor, enzyme, nucleic acid or other target and the like.

The term "aliphatic" is art-recognized and refers to a linear, branched, cyclic alkane, alkene, or alkyne. In certain embodiments, aliphatic groups may be linear or branched and have from 1 to about 20 carbon atoms.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure. The term "alkyl" is also defined to include halosubstituted alkyls.

The term "aralkyl" is art-recognized and refers to an alkyl group substituted with an aryl group (e.g., an aromatic or heteroaromatic group).

The terms "alkenyl" and "alkynyl" are art-recognized and refer to unsaturated aliphatic groups analogous in length and possible substitution to the alkyls described above, but that contain at least one double or triple bond respectively.

Unless the number of carbons is otherwise specified, "lower alkyl" refers to an alkyl group, as defined above, but having from one to about ten carbons, alternatively from one to about six carbon atoms in its backbone structure. Likewise, "lower alkenyl" and "lower alkynyl" have similar chain lengths.

The term "heteroatom" is art-recognized and refers to an atom of any element other than carbon or hydrogen. Illustrative heteroatoms include boron, nitrogen, oxygen, phosphorus, sulfur and selenium.

The term "aryl" is art-recognized and refers to 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "heteroaryl." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" are art-recognized and refer to 3- to about 10-membered ring structures, alternatively 3- to about 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxanthene, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The terms "polycyclyl" or "polycyclic group" are art-recognized and refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The term "carbocycle" is art-recognized and refers to an aromatic or non-aromatic ring in which each atom of the ring is carbon.

The term "nitro" is art-recognized and refers to —NO$_2$; the term "halogen" is art-recognized and refers to —F, —Cl, —Br or —I; the term "sulfhydryl" is art-recognized and refers to —SH; the term "hydroxyl" means —OH; and the term "sulfonyl" is art-recognized and refers to —SO$_2$. "Halide" designates the corresponding anion of the halogens, and "pseudohalide" has the definition set forth on page 560 of "*Advanced Inorganic Chemistry*" by Cotton and Wilkinson.

The terms "amine" and "amino" are art-recognized and refer to both unsubstituted and substituted amines, e.g., a moiety that may be represented by the general formulas:

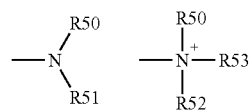

wherein R50, R51 and R52 each independently represent a hydrogen, an alkyl, an alkenyl, —(CH$_2$)$_m$—R61, or R50 and R51, taken together with the N atom to which they are attached complete a heterocycle having from 4 to 8 atoms in the ring structure; R61 represents an aryl, a cycloalkyl, a cycloalkenyl, a heterocycle or a polycycle; and m is zero or an integer in the range of 1 to 8. In certain embodiments, only one of R50 or R51 may be a carbonyl, e.g., R50, R51 and the nitrogen together do not form an imide. In other embodiments, R50 and R51 (and optionally R52) each independently represent a hydrogen, an alkyl, an alkenyl, or —(CH$_2$)$_m$—R61. Thus, the term "alkylamine" includes an amine group, as defined above, having a substituted or unsubstituted alkyl attached thereto, i.e., at least one of R50 and R51 is an alkyl group.

The term "acylamino" is art-recognized and refers to a moiety that may be represented by the general formula:

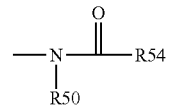

wherein R50 is as defined above, and R54 represents a hydrogen, an alkyl, an alkenyl or —(CH$_2$)$_m$—R61, where m and R61 are as defined above.

The term "amido" is art recognized as an amino-substituted carbonyl and includes a moiety that may be represented by the general formula:

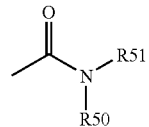

wherein R50 and R51 are as defined above. Certain embodiments of the amide described herein will not include imides which may be unstable.

The term "alkylthio" refers to an alkyl group, as defined above, having a sulfur radical attached thereto. In certain embodiments, the "alkylthio" moiety is represented by one of —S-alkyl, —S-alkenyl, —S-alkynyl, and —S—(CH$_2$)$_m$—R61, wherein m and R61 are defined above. Representative alkylthio groups include methylthio, ethyl thio, and the like.

The term "carbonyl" is art recognized and includes such moieties as may be represented by the general formulas:

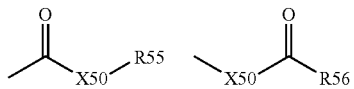

wherein X50 is a bond or represents an oxygen or a sulfur, and R55 and R56 represents a hydrogen, an alkyl, an alkenyl, —(CH$_2$)$_m$—R61 or a pharmaceutically acceptable salt, R56 represents a hydrogen, an alkyl, an alkenyl or —(CH$_2$)$_m$—R61, where m and R61 are defined above. Where X50 is an oxygen and R55 or R56 is not hydrogen, the formula represents an "ester". Where X50 is an oxygen, and R55 is as defined above, the moiety is referred to herein as a carboxyl group, and particularly when R55 is a hydrogen, the formula represents a "carboxylic acid". Where X50 is an oxygen, and R56 is hydrogen, the formula represents a "formate". In general, where the oxygen atom of the above formula is replaced by sulfur, the formula represents a "thiolcarbonyl" group. Where X50 is a sulfur and R55 or R56 is not hydrogen, the formula represents a "thiolester." Where X50 is a sulfur and R55 is hydrogen, the formula represents a "thiolcarboxylic acid." Where X50 is a sulfur and R56 is hydrogen, the formula represents a "thiolformate." On the other hand, where X50 is a bond, and R55 is not hydrogen, the above formula represents a "ketone" group. Where X50 is a bond, and R55 is hydrogen, the above formula represents an "aldehyde" group.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O—(CH$_2$)$_m$—R61, where m and R61 are described above.

The term "sulfonate" is art recognized and refers to a moiety that may be represented by the general formula:

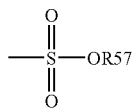

in which R57 is an electron pair, hydrogen, alkyl, cycloalkyl, or aryl.

The term "sulfate" is art recognized and includes a moiety that may be represented by the general formula:

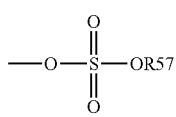

in which R57 is as defined above.

The term "sulfonamido" is art recognized and includes a moiety that may be represented by the general formula:

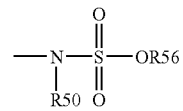

in which R50 and R56 are as defined above.

The term "sulfamoyl" is art-recognized and refers to a moiety that may be represented by the general formula:

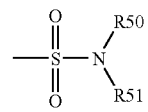

in which R50 and R51 are as defined above.

The term "sulfonyl" is art-recognized and refers to a moiety that may be represented by the general formula:

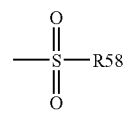

in which R58 is one of the following: hydrogen, alkyl, alkenyl, alkynyl, cycloalkyl, heterocyclyl, aryl or heteroaryl.

The term "sulfoxido" is art-recognized and refers to a moiety that may be represented by the general formula:

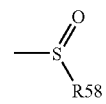

in which R58 is defined above.

The term "phosphoryl" is art-recognized and may in general be represented by the formula:

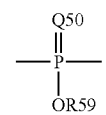

wherein Q50 represents S or O, and R59 represents hydrogen, a lower alkyl or an aryl. When used to substitute, e.g., an alkyl, the phosphoryl group of the phosphorylalkyl may be represented by the general formulas:

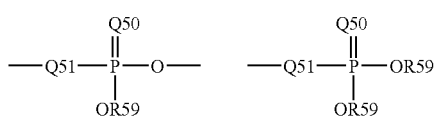

wherein Q50 and R59, each independently, are defined above, and Q51 represents O, S or N. When Q50 is S, the phosphoryl moiety is a "phosphorothioate".

The term "phosphoramidite" is art-recognized and may be represented in the general formulas:

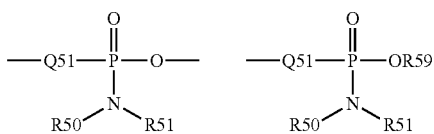

wherein Q51, R50, R51 and R59 are as defined above.

The term "phosphonamidite" is art-recognized and may be represented in the general formulas:

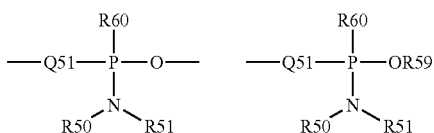

wherein Q51, R50, R51 and R59 are as defined above, and R60 represents a lower alkyl or an aryl.

Analogous substitutions may be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The definition of each expression, e.g. alkyl, m, n, and the like, when it occurs more than once in any structure, is intended to be independent of its definition elsewhere in the same structure.

The term "selenoalkyl" is art-recognized and refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—R61, m and R61 being defined above.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*.

Certain compounds contained in compositions described herein may exist in particular geometric or stereoisomeric forms. In addition, polymers described herein may also be optically active. Contemplated herein are all such compounds, including cis- and trans-isomers, R- and S-enantiomers, diastereomers, (D)-isomers, (L)-isomers, the racemic mixtures thereof, and other mixtures thereof. Additional asymmetric carbon atoms may be present in a substituent such as an alkyl group. All such isomers, as well as mixtures thereof, are intended to be included in the compositions described herein.

If, for instance, a particular enantiomer of a compound described herein is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. In certain embodiments, heteroatoms such as nitrogen may have hydrogen substituents and/or any permissible substituents of organic compounds described herein which satisfy the valences of the heteroatoms. Permissible substituents of organic compounds are not intended to be limited in any manner by the instant description.

Chemical elements may be identified in accordance with the Periodic Table of the Elements, CAS version, *Handbook of Chemistry and Physics*, 67th Ed., 1986-87, inside cover. Additionally, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds that may be substituted or unsubstituted.

The term "protecting group" is art-recognized and refers to temporary substituents that protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed by Greene and Wuts in *Protective Groups in Organic Synthesis* (2nd ed., Wiley: New York, 1991).

The term "hydroxyl-protecting group" is art-recognized and refers to those groups intended to protect a hydroxyl group against undesirable reactions during synthetic procedures and includes, for example, benzyl or other suitable esters or ethers groups known in the art.

The term "carboxyl-protecting group" is art-recognized and refers to those groups intended to protect a carboxylic acid group, such as the C-terminus of an amino acid or peptide or an acidic or hydroxyl azepine ring substituent, against undesirable reactions during synthetic procedures and includes. Examples for protecting groups for carboxyl groups involve, for example, benzyl ester, cyclohexyl ester, 4-nitrobenzyl ester, t-butyl ester, 4-pyridylmethyl ester, and the like.

The term "amino-blocking group" is art-recognized and refers to a group which will prevent an amino group from participating in a reaction carried out on some other functional group, but which can be removed from the amine when desired. Such groups are discussed by in Ch. 7 of Greene and Wuts, cited above, and by Barton, *Protective Groups in Organic Chemistry* ch. 2 (McOmie, ed., Plenum Press, New York, 1973). Examples of suitable groups include acyl protecting groups such as, to illustrate, formyl, dansyl, acetyl, benzoyl, trifluoroacetyl, succinyl, methoxysuccinyl, benzyl and substituted benzyl such as 3,4-dimethoxybenzyl, o-nitrobenzyl, and triphenylmethyl; those of the formula —COOR where R includes such groups as methyl, ethyl, propyl, isopropyl, 2,2,2-trichloroethyl, 1-methyl-1-phenylethyl, isobutyl, t-butyl, t-amyl, vinyl, allyl, phenyl, benzyl, p-nitrobenzyl, o-nitrobenzyl, and 2,4-dichlorobenzyl; acyl groups and substituted acyl such as formyl, acetyl, chloroacetyl, dichloroacetyl, trichloroacetyl, trifluoroacetyl, benzoyl, and p-methoxybenzoyl; and other groups such as methanesulfonyl, p-toluenesulfonyl, p-bromobenzenesulfonyl, p-nitrophenylethyl, and p-toluenesulfonyl-aminocarbonyl. Preferred amino-blocking groups are benzyl (—$CH_2C_6H_5$), acyl [C(O)R1] or $SiR1_3$ where R1 is $C_1$-$C_4$ alkyl, halomethyl, or 2-halo-substituted-($C_2$-$C_4$ alkoxy), aromatic urethane protecting groups as, for example, carbonylbenzyloxy (Cbz); and aliphatic urethane protecting groups such as t-butyloxycarbonyl (Boc) or 9-fluorenylmethoxycarbonyl (FMOC).

The definition of each expression, e.g. lower alkyl, m, n, p and the like, when it occurs more than once in any structure, is intended to be independent of its definition elsewhere in the same structure.

The term "electron-withdrawing group" is art-recognized, and refers to the tendency of a substituent to attract valence electrons from neighboring atoms, i.e., the substituent is electronegative with respect to neighboring atoms. A quantification of the level of electron-withdrawing capability is given by the Hammett sigma (a) constant. This well known constant is described in many references, for instance, March, *Advanced Organic Chemistry* 251-59 (McGraw Hill Book Company: New York, 1977). The Hammett constant values are generally negative for electron donating groups ($\sigma(P)$=–0.66 for $NH_2$) and positive for electron withdrawing groups ($\sigma(P)$=0.78 for a nitro group), $\sigma(P)$ indicating para substitution. Exemplary electron-withdrawing groups include nitro, acyl, formyl, sulfonyl, trifluoromethyl, cyano, chloride, and the like. Exemplary electron-donating groups include amino, methoxy, and the like.

The term "modulation", when used in reference to a functional property or biological activity or process (e.g., enzyme activity or receptor binding), refers to the capacity to either up regulate (e.g., activate or stimulate), down regulate (e.g., inhibit or suppress) or otherwise change a quality of such property, activity or process. In certain instances, such regulation may be contingent on the occurrence of a specific event, such as activation of a signal transduction pathway, and/or may be manifest only in particular cell types.

The term "treating" is art-recognized and refers to curing as well as ameliorating at least one symptom of any condition or disease. In an exemplary embodiment, treating of a pregnancy disorder, includes, for example, inhibiting the disease or disorder, e.g., arresting its development, or ameliorating or relieving at least one symptom of the disease or disorder, e.g., causing regression of the pregnancy disorder.

The term "prophylactic" or "therapeutic" treatment of a pregnancy disorder refers to administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if administered after manifestation of the unwanted condition, the treatment is therapeutic (i.e., it is intended to diminish, ameliorate or maintain the existing unwanted condition or side effects therefrom).

A "patient," "subject" or "host" to be treated by the subject method may mean either a human or non-human animal.

The term "mammal" is known in the art, and exemplary mammals include humans, primates, bovines, porcines, canines, felines, and rodents (e.g., mice and rats).

The term "bioavailable" in the context of a compound is art-recognized and refers to a form of the compound that allows for it, or a portion of the amount administered, to be absorbed by, incorporated to, or otherwise physiologically available to a subject or patient to whom it is administered.

The term "pharmaceutically-acceptable salts" is art-recognized and refers to the relatively non-toxic, inorganic and organic acid addition salts of compounds, including, for example, those contained in compositions described herein.

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any subject composition or component thereof from one organ, or portion of the body, to another organ, or portion of the body. Each carrier must be "acceptable" in the sense of being compatible with a subject composition and its components and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The terms "systemic administration," "administered systemically," "peripheral administration" and "administered peripherally" are art-recognized and refer to the administration of a subject composition, therapeutic or other material other than directly into the central nervous system, such that it enters the patient's system and, thus, is subject to metabolism and other like processes, for example, subcutaneous administration.

The terms "parenteral administration" and "administered parenterally" are art-recognized and refer to modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intra-articulare, subcapsular, subarachnoid, intraspinal, and intrasternal injection and infusion.

Contemplated equivalents of the compositions described herein include compositions which otherwise correspond thereto, and which have the same general properties thereof, wherein one or more simple variations of substituents or components are made which do not adversely affect the characteristics of the compositions of interest. In general, the components of the compositions described herein may be prepared using readily available starting materials, reagents and conventional synthesis procedures. In these reactions, it is also possible to make use of variants which are in themselves known, but are not mentioned here.

Methods

Provided herein are methods and compositions for treating, preventing and/or diagnosing a pregnancy disorder. In one embodiment, methods and compositions for treating or preventing a pregnancy disorder using 2-methoxyestradiol, or an analog thereof, are provided. In another embodiment, methods for diagnosing a pregnancy disorder by determining the level of 2-methoxyestradiol (or a precursor or metabolite thereof) in a pregnant subject are provided. In an exemplary embodiment, the methods and compositions described herein may be used for treating or preventing preeclampsia by administering 2-methoxyestradiol, or an analog of 2-methoxyestradiol, to a subject in need thereof. In another exemplary embodiment, the methods and compositions described herein may be used for diagnosing preeclampsia, or the likelihood of developing preeclampsia, comprising detecting the level of 2-methoxyestradiol (or a precursor or metabolite thereof) in a pregnant subject.

In certain embodiments, the methods described herein may involve first identifying a subject susceptible to, or suffering from, a pregnancy disorder. Subjects susceptible to, or suffering from, a pregnancy disorder may be identified by recognizing symptoms of a pregnancy disorder that are being exhibited by the patient. Alternatively, subjects susceptible to, or suffering from, a pregnancy disorder may be identified by determining the level of 2-methoxyestradiol (or a precursor or metabolite thereof) in a subject and comparing that level to a control. Any deviation from the control level of 2-methoxyestradiol (or a precursor or metabolite thereof) may be indicative of a subject suffering from a pregnancy disorder. In an exemplary embodiment, pregnant subjects may be screened for levels of 2-methoxyestradiol (or a precursor or metabolite thereof) on a regular basis (or at regular intervals) for purposes of diagnosis of a pregnancy disorder or to monitor the stage or development of a pregnancy disorder. In one embodiment, screening for levels of 2-methoxyestradiol (or a precursor or metabolite thereof) may be carried out about once every trimester, once every month, once every 3 weeks, once every 2 weeks, once every 10 days, once every week, or about once every 144, 120, 96, 72, 48, 24, or 12 hours. In another embodiment, pregnant subjects may be screened on a regular basis throughout pregnancy or on a regular basis during one or more stages of pregnancy, such as, for example, screening on a regular basis during the first, second and/or third trimesters of pregnancy. In yet another embodiment, subjects may be screened for levels of 2-methoxyestradiol (or precursors or metabolites thereof) after delivery or termination of a pregnancy in order to identify or monitor diseases or disorders associated with the prior pregnancy, such as, for example, a retained placenta. In an exemplary embodiment, screening for levels of 2-methoxyestradiol (or precursors or metabolites thereof) may be used to identify subjects that may be candidates for therapeutic treatment with 2-methoxyestradiol, or an analog thereof. In another embodiment, screening for levels of 2-methoxyestradiol (or precursors or metabolites thereof) may be used to calculate an effective dose for administering to a pregnant subject.

Subjects identified as having a lower level or a higher level of 2-methoxyestradiol as compared to a control may be susceptible to, or suffering from, a pregnancy disorder. In one embodiment, subjects having a low level of 2-methoxyestradiol as compared to a control may be susceptible to, or suffering from, one or more of the following pregnancy disorders: preeclampsia, eclampsia, hypertension, edema, IUGR (Intrauterine Growth Retardation), HELPP syndrome (Hemolysis, Elevated Liver Enzymes, and Low Platelet count), placental separation, placenta previa, ectopic pregnancy, or retained placenta. In an exemplary embodiment, subjects suffering from preeclampsia may be diagnosed or monitored by detecting a low level of 2-methoxyestradiol in the subject as compared to a control during the first, second and/or third trimester of pregnancy. Alternatively, subjects having a high level of 2-methoxyestradiol, particularly in the first trimester, as compared to a control may be susceptible to miscarriage.

The degree or severity of a pregnancy disorder may be determined based on the degree of deviation in the level of 2-methoxyestradiol in a subject as compared to a control. For example, a subject exhibiting a greater deviation in the level of 2-methoxyestradiol as compared to a control may indicate that the subject is more susceptible to, or suffering from a more severe case of, a pregnancy disorder.

Screening for levels of 2-methoxyestradiol (or precursors or metabolites thereof) may be used to monitor the course of treatment with 2-methoxyestradiol, or an analog thereof. When treating a subject with an analog of 2-methoxyestradiol it may be useful for monitoring purposes to determine the level of 2-methoxyestradiol (or a precursor or metabolite thereof) and/or the level of the 2-methoxyestradiol analog (or a precursor or analog thereof). In an exemplary embodiment, it may be useful to determine the level of 2-methoxyestradiol plus the level of a 2-methoxyestradiol analog being administered to a subject. In another embodiment, it may be useful to determine the level of a precursor of 2-methoxyestradiol plus the level of a precursor a 2-methoxyestradiol analog. In yet another embodiment, it may be useful to determine the level of a metabolite of 2-methoxyestradiol plus the level of a metabolite of a 2-methoxyestradiol analog.

The level of 2-methoxyestradiol in a subject may be determined directly by measuring the level of 2-methoxyestradiol itself. Alternatively, the level of 2-methoxyestradiol may be determined indirectly by measuring the level of a precursor or a metabolite of 2-methoxyestradiol. Similarly, the level of an analog of 2-methoxyestradiol may be determined by directly measuring the level of the analog in a subject or indirectly by measuring the level of a precursor or metabolite of the analog. In yet another embodiment, the level of a precursor or a metabolite of 2-methoxyestradiol, or an analog thereof, may be measured directly for diagnostic or monitoring purposes. In this instance, the precursor or analite is not being used as a proxy for the level of 2-methoxyestradiol, or an analog thereof, but rather is being used directly for diagnostic or monitoring purposes.

The level of 2-methoxyestradiol, or an analog thereof, may be determined in a biologic sample of a subject or a control subject. In an exemplary embodiment, the level of 2-methoxyestradiol may be determined in a urine, blood or plasma sample from a subject.

The level of 2-methoxyestradiol, or analog thereof, in a biological sample of a subject may be compared directly to a control. In another embodiment, the level of 2-methoxyestradiol, or analog thereof, in a biological sample of a subject may be used to calculate the physiological concentration of 2-methoxyestradiol, or analog thereof, found in a subject. The physiological concentration of the 2-methoxyestradiol, or analog thereof, in a subject may then optionally be compared to a control.

The level of 2-methoxyestradiol (or a precursor or metabolite thereof) or an analog of 2-methoxyestradiol (or a precursor or metabolite thereof) may be determined using a method known in the art. For example, the level of 2-methoxyestradiol and/or analogs thereof (and precursors or metabolites thereof) in a sample may be determined using thin layer chromatography. Alternatively, the level of 2-methoxyestradiol and/or analogs thereof (and precursors or metabolites thereof) may be determined using immunoassays.

The level of 2-methoxyestradiol, or an analog thereof, in a subject may be compared to a control either quantitatively or qualitatively. For example, a qualitative (or unitless) comparison may be carried out by determining whether the level of 2-methoxyestradiol, or an analog thereof, in a subject is higher, lower, or about the same as a control. Optionally, a qualitative comparison may be used to estimate the magnitude of difference in the level of 2-methoxyestradiol, or an analog thereof, in a subject as compared to a control, such as, for example, a 2-fold change, a 50% change, etc. A quantitative comparison may be carried out by determining the quantity of 2-methoxyestradiol, or an analog thereof, in a subject as compared to the quantity in a control, wherein the quantity has some form of units attached (such as, for example, mg of protein, volume of a spot/band in a gel, intensity of a spot on a phosphoimager or autoradiogram exposure, volume of a spot on a chromatography plate, etc.).

It may be desirable to monitor symptoms of a pregnancy disorder in addition to, or instead of, monitoring the level of 2-methoxyestradiol (or a precursor or metabolite thereof) in a subject. For example, in a subject suffering from or susceptible to preeclampsia, it may be desirable to monitor the blood pressure and/or level of protein in the urine of the subject before, during and/or after treatment with the subject 2-methoxyestradiol, or an analog thereof. In exemplary embodiments, it may be desirable to determine the blood pressure of a subject on a regular basis (e.g., hourly, daily, weekly, monthly, etc.) in order to monitor the course of treatment and/or design a treatment strategy. Blood pressure may be monitoring using any technique known in the art, such as, for example, a Finometer (TNO Biomedical Instruments, Amsterdam, The Netherlands) or a sphygmometer. Urinary protein excretion may be measured by any method known in the art, including, for example, by spectrophotometric assays using a bicinchoninic acid reagent (Pierce, Rockford, Ill.).

In one embodiment, the methods described herein involve administering 2-methoxyestradiol to a subject. Alternatively, it may be desirable to administer a mixture of 2-methoxyestradiol and one or more analogs of 2-methoxyestradiol, or a mixture of two or more analogs of 2-methoxyestradiol, to a subject. In other embodiments, it may be desirable to administer 2-methoxyestradiol and/or an analog(s) thereof to a subject in combination with another therapeutic agent effective for treating or ameliorating at least one symptom of a pregnancy disorder. In an exemplary embodiment, 2-methoxyestradiol is administered with another therapeutic agent effective for treating or ameliorating a symptom of preeclampsia, such as, for example, an anti-hypertensive and/or an anticonvulsant agent. Examples of suitable hypertensive agent for use in association with the methods and compositions described herein, include, for example, hydralazine (Apresoline), labetalol (Normodyne) and Nitroprusside (Nitropress). Suitable anticonvulsant agents for use in the methods and compositions described herein are magnesium sulfate, Phenytoin (Dilantin), and Diazepam (Valium). In embodiments directed to combination therapies, the drugs may be formulated and administered together as a mixture or may be separately formulated and administered.

In an exemplary embodiment, a subject susceptible to, or suffering from, a pregnancy disorder associated with a low level of 2-methoxyestradiol is administered an amount of 2-methoxyestradiol, or an analog thereof, sufficient to raise the level of 2-methoxyestradiol (or the level of 2-methoxyestradiol plus the level of a 2-methoxyestradiol analog) up to about the level of 2-methoxyestradiol in a control subject. In a further embodiment, a subject may be administered on a regular basis an amount of 2-methoxyestradiol, or an analog thereof, sufficient to maintain the level of 2-methoxyestradiol (or the level of 2-methoxyestradiol plus the level of a 2-methoxyestradiol analog) in the subject at about a control level. For example, in certain embodiments, it may be desirable to administer 2-methoxyestradiol and/or an analog thereof to a subject on a monthly, weekly, or daily basis. In an exemplary embodiment, the level of 2-methoxyestradiol (or the level of 2-methoxyestradiol plus the level of a 2-methoxyestradiol analog) is maintained in a subject at about a control level throughout pregnancy. In order to maintain an appropriate level of 2-methoxyestradiol (or the level of 2-methoxyestradiol plus the level of a 2-methoxyestradiol analog) in a subject it may be desirable to regularly monitor the subject for levels of 2-methoxyestradiol (or the level of 2-methoxyestradiol plus the level of a 2-methoxyestradiol analog) and adjust the amount of therapeutic agent administered to the subject accordingly.

In one embodiment, a 2-methoxyestradiol analog suitable for use in accordance with the methods and compositions described herein comprise a compound of formula I:

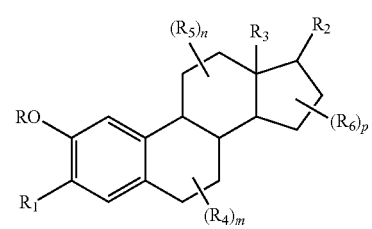

wherein, independently for each occurrence:
R is H, $C_{1-6}$ alkyl, aryl, aralkyl, or carbonyl;
$R_1$ and $R_2$ are —OR, —SR, or —N(R)$_2$;
$R_3$ is H, halide, $C_{1-6}$ alkyl, aryl, aralkyl, or carbonyl;
$R_4$, $R_5$, and $R_6$ is are H, halide, $C_{1-6}$ alkyl, aryl, aralkyl, or carbonyl;
m is an integer from 1-5 inclusive; and
n and p are an integer from 1-6 inclusive.

In a further embodiment, a 2-methoxyestradiol analog suitable for use in accordance with the methods and compositions described herein comprise a compound of formula I and the attendant definitions, wherein R is methyl.

In a further embodiment, a 2-methoxyestradiol analog suitable for use in accordance with the methods and compositions described herein comprise a compound of formula I and the attendant definitions, wherein $R_1$ is OH.

In a further embodiment, a 2-methoxyestradiol analog suitable for use in accordance with the methods and compositions described herein comprise a compound of formula I and the attendant definitions, wherein $R_2$ is OH.

In a further embodiment, a 2-methoxyestradiol analog suitable for use in accordance with the methods and compositions described herein comprise a compound of formula I and the attendant definitions, wherein $R_3$ is methyl.

In a further embodiment, a 2-methoxyestradiol analog suitable for use in accordance with the methods and compositions described herein comprise a compound of formula I and the attendant definitions, wherein $R_4$ is H.

In a further embodiment, a 2-methoxyestradiol analog suitable for use in accordance with the methods and compositions described herein comprise a compound of formula I and the attendant definitions, wherein $R_5$ is H.

In a further embodiment, a 2-methoxyestradiol analog suitable for use in accordance with the methods and compositions described herein comprise a compound of formula I and the attendant definitions, wherein $R_6$ is H.

In a further embodiment, a 2-methoxyestradiol analog suitable for use in accordance with the methods and compositions described herein comprise a compound of formula I and the attendant definitions, wherein R is methyl and $R_1$ is OH.

In a further embodiment, a 2-methoxyestradiol analog suitable for use in accordance with the methods and compositions described herein comprise a compound of formula I and the attendant definitions, wherein R is methyl and $R_2$ is OH.

In a further embodiment, a 2-methoxyestradiol analog suitable for use in accordance with the methods and compositions described herein comprise a compound of formula I and the attendant definitions, wherein R is methyl and $R_3$ is methyl.

In a further embodiment, a 2-methoxyestradiol analog suitable for use in accordance with the methods and compositions described herein comprise a compound of formula I and the attendant definitions, wherein R is methyl, $R_1$ is OH, and $R_2$ is OH.

In a further embodiment, a 2-methoxyestradiol analog suitable for use in accordance with the methods and compositions described herein comprise a compound of formula I and the attendant definitions, wherein R is methyl, $R_1$ is OH, $R_2$ is OH, and $R_3$ is methyl.

In a further embodiment, a 2-methoxyestradiol analog suitable for use in accordance with the methods and compositions described herein comprise a compound of formula I and the attendant definitions, wherein $R_4$, $R_5$, and $R_6$ are H.

In a further embodiment, a 2-methoxyestradiol analog suitable for use in accordance with the methods and compositions described herein comprise a compound of formula I and the attendant definitions, wherein R is methyl, and $R_4$, $R_5$, and $R_6$ are H.

In a further embodiment, a 2-methoxyestradiol analog suitable for use in accordance with the methods and compositions described herein comprise a compound of formula I and the attendant definitions, wherein R is methyl, $R_1$ is OH, and $R_4$, $R_5$, and $R_6$ are H.

In a further embodiment, a 2-methoxyestradiol analog suitable for use in accordance with the methods and compositions described herein comprise a compound of formula I and the attendant definitions, wherein R is methyl, $R_1$ is OH, $R_2$ is OH, and $R_4$, $R_5$, and $R_6$ are H.

In a further embodiment, a 2-methoxyestradiol analog suitable for use in accordance with the methods and compositions described herein comprise a compound of formula I and the attendant definitions, wherein R is methyl, $R_1$ is OH, $R_2$ is OH, $R_3$ is methyl, and $R_4$, $R_5$, and $R_6$ are H.

Also included in the compositions and methods described herein are pharmaceutically acceptable addition salts and complexes of formula I. In cases wherein the compounds may have one or more chiral centers, unless specified, the compositions described herein comprise each unique racemic compound, as well as each unique nonracemic compound.

In cases in which the compounds have unsaturated carbon-carbon double bonds, both the cis (Z) and trans (E) isomers are intended to be included in association with the compounds described herein. In cases wherein the compounds may exist in tautomeric forms, such as keto-enol tautomers, such as

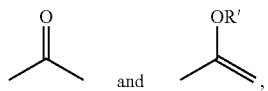

each tautomeric form is intended to be included in association with the compounds described herein, whether existing in equilibrium or locked in one form by appropriate substitution with R'. The meaning of any substituent at any one occurrence is independent of its meaning, or any other substituent's meaning, at any other occurrence.

Also included in the methods and compositions described herein are prodrugs of 2-methoxyestradiol and the compounds of formula I.

The compounds of formula I may be prepared by any conventional method useful for the preparation of analogous compounds. Starting materials for the processes are known or can be prepared by known processes from commercially available materials. A compound used in the methods described herein can be converted to another compound used in the methods described herein using conventional methods. The products of the reactions are isolated by conventional means such as extraction, crystallization, distillation, chromatography, and the like.

Known compounds that are used in accordance with the invention and precursors to novel compounds according to the invention can be purchased, e.g., from Sigma Chemical Co., St. Louis, Steraloids and Research Plus. Other compounds according to the invention can be synthesized according to known methods from publicly available precursors.

The chemical synthesis of estradiol has been described (Eder, V. et al., Ber 109, 2948 (1976); Oppolzer, D. A. and Roberts, D A. Helv. Chim. Acta. 63, 1703, (1980)). The synthetic pathways used to prepare some of the 2-methoxyestradiol analogs of the present invention are based on modified published literature procedures for estradiol derivatives and dimethylhydrazone (Trembley et al., Bioorganic & Med. Chem. 1995 3, 505-523; Fevig et al., J. Org. Chem., 1987 52, 247-251; Gonzalez et al., Steroids 1982, 40, 171-187; Trembley et al., Synthetic Communications 1995, 25, 2483-2495; Newkome et al., J. Org. Chem. 1966, 31, 677-681; Corey et al Tetrahedron Lett 1976, 3-6; Corey et al., Tetrahedron Lett, 1976, 3667-3668) and German Patent No. 2757157 (1977).

In exemplary embodiments, 2-methoxyestradiol analogs suitable for use with the compositions and methods described herein are described in U.S. Pat. No. 6,528,676, and U.S. Patent Application Publication Nos. 2003/0236408, 2002/0147183, 2003/0187076, 2002/0082433, and 2003/0236439. 2-methoxyestradiol, or analogs thereof, may be purchased from commercially available sources or may be prepared as described in, for example, U.S. Pat. No. 6,528,676, and U.S. Patent Application Publication Nos. 2003/0236408, 2002/0147183, 2003/0187076, 2002/0082433, and 2003/0236439. Examples of 2-methoxyestradiol analogs suitable for use in accordance with the methods and compositions described herein include one or more of the following: 17 substituted 2-methoxyestradiol derivatives: estra-1,3,5(10)-triene-3, 17α-diol, 2-methoxyestra-1,3,5(10)-triene-3-ol, 17β-aminoestra-1,3,5,(10)-triene-3,17β-diol, 2-methoxy-17-oxime-3-hydroxyestra-1,3,5(10)-triene-17-one, 2-methoxy-3,17β-bis(acetyloxy)estra-1,3,5,(10)-triene, 2-methoxy-17β-propaneestra-1,3,5(10)-triene-3-ol, 2-methoxy-17β- methylestra-1,3,5(10)-triene-3-ol, 2-methoxy-17(20)-Z-propylideneestra-1,3,5,(10)-triene-3-ol, 17(20)-methyleneestra-1,3,5(10)-triene-3-ol, 2-methoxy-17β-(N-n-(1)propylamino)estra-1,3,5(10)-triene-3-ol, 2-methoxy-19-norpregna-1,3,5(10)17(20)-tetraen-3-ol, 2-methoxy-17β-ethylestra-1,3,5(10)-triene-3-ol, 2-methoxy-17-(4-tosylhydrazone)estra-1,3,5(10)-triene-3-ol, 2-methoxy-17(20)-Z-butylideneestra-1,3,5(10)-triene-3-ol, 2-methoxy-17β-butylestra-1,3,5(10)-triene-3-ol; 2 substituted estradiol derivatives: 2-acetylestra-1,3,5(10)-triene-3,17β-diol, 2-formylestra-1,3,5(10)-triene-3,17β-diol, 2-(hydroxymethyl)estra-1,3,5(10)-triene-3,17β-diol, 2-ethylestra-1,3,5(10)-triene-3,17β-diol, 2-methylestra-1,3,5(10)-triene-3,17β-diol, 2-nitroestra-1,3,5(10)-triene-3,17β-diol, 2-(N,N-dimethylamino) estra-1,3,5(10)-triene-3,17β-diol, 2-aminoestra-1,3,5(10)-triene-3-ol, 2-formamideestra-1,3,5(10)-triene-3-ol, 2-(N-methylamino)estra-1,3,5(10)-triene-3-ol-HCl, 2-(N,N-dimethylamino)estra-1,3,5(10)-triene-3-ol, 2-(N,N-dimethylamino)estra-1,3,5(10)-triene-3-ol-HCL, 2-aminoestra-1,3,5(10)-triene-3,17β-diol, 2-(N,N-dimethylamino)-17(20)-methyleneestra-1,3,5(10)-triene-3-ol-HCL, 2-(1'-propynyl)estra-1,3,5(10)-triene-3,17β-diol, 2-Azidoestra 1,3,5(10)-triene-3,17β-diol, 2-ethoxyestra-1,3,5(10)-triene-3,17β-diol, estra-1,3,5(10)-triene-3-ol; 16 substituted 2-methoxyestradiol derivatives: 2-methoxy-16α-methylestra-1,3,5(10)-triene-3,17β-diol, 2-methoxy-16β-methylestra-1,3,5(10)-triene-3,17β-diol, 2-methoxy-16-ethylestra-1,3,5,(10)-triene-3,17β-diol, 16β-(hydroxymethyl)estra-1,3,5(10)-triene-3,17β-diol, 16α(hydroxymethyl)estra-1,3,5(10)-triene-3,17β-diol, 2-methoxy-16α-propaneestra-1,3,5(10)-triene-3,17β-diol, 2-methoxy-16β-propaneestra-1,3,5(10)-triene-3,17β-diol, 2-methoxy-16β-butaneestra-1,3,5(10)-triene-3,17β-diol, 2-methoxy-16α-butaneestra-1,3,5(10)-triene-3,17β-diol, 2-methoxy-16β-iso-butaneestra-1,3,5(10)-triene-3,17β-diol, 2-methoxy-16α-(N,N-dimethylaminomethyl)estra-1,3,5(10)-triene-3,17β-diol, 2-methoxy-16α-ethylestra-1,3,5(10)-triene-3,17β-diol; dehydrogenated/substituted 2-methoxyestradiol derivatives: 2-methoxy-estra-1,3,5(10)9(11)-tetraene-3,17β-diol; other 2-methoxyestradiol derivatives: 2-ethoxy-19-norpregnane-1,3,5(10)17(20)-tetraen-3-ol, 2-(1-propynyl)-19-norpregnane-1,3,5(10)17(20)-tetraen-3-ol, 2-formyl-19-norpregnane-1,3,5(10)17(20)-tetraen-3-ol, 2-formamide-19-norpregnane-1,3,5(10)17(20)-tetraen-3-ol, 2-methyenehydroxy-19-norpregnane-1,3,5(10)17(20)-tetraen-3-ol, 2-ethyl-19-norpregnane-1,3,5(10)17(20)-tetraen-3-ol, 2-methyl-19-norpregnane-1,3,5(10)17(20)-tetraen-3-ol, 2-(1-propenyl)-19-norpregnane-1,3,5(10)17(20)-tetraen-3-ol, 2-ethoxy-17(20)-methyleneestra-1,3,5(10)-triene-3-ol, 2-(1-propynyl)-17(20)-methyleneestra-1,3,5(10)-triene-3-ol, 2-formyl-17(20)-methyleneestra-1,3,5(10)-triene-3-ol, 2-formamide-17(20)-methyleneestra-1,3,5(10)-triene-3-ol, 2-methylenehydroxy-17(20)-metlyneestra-1,3,5(10)-triene-3-ol, 2-ethyl-17(20)-methyleneestra-1,3,5(10)-triene-3-ol, 2-methyl-17(20)-methyleneestra-1,3,5(10)-triene-3-ol, 2-(1-propenyl)-17(20)-methyleneestra-1,3,5(10)-triene-3-ol, 2-ethoxyestra-1,3,5(10)-triene-3-ol, 2-(1-propynyl)estra-1,3,5(10)-triene-3-ol, 2-formylestra-1,3,5(10)-triene-3-ol, 2-formamideestra-1,3,5(10)-triene-3-ol, 2-(methylenehydroxy)estra-1,3,5(10)-triene-3-ol, 2-ethylestra-1,3,5(10)-triene-3-ol, 2-methylestra-1,3,5(10)-triene-3-ol, 2-(1-propenyl)estra-1,3,5(10)-triene-3-ol, 2-ethoxy-17β-methylestra-1,3,5(10)-triene-3-ol, 2-(1-propynyl)-17β-methylestra-1,3,5(10)-triene-3-ol, 2-formyl-17β-methylestra-1,3,5(10)-triene-3-ol, 2-formamide-17β-methylestra-1,3,5(10)-triene-3-ol, 2-methylenehydroxy-17β-methylestra-1,3,5(10)-triene-3-ol, 2-ethyl-17β-methylestra-1,3,5(10)-triene-3-ol, 2-methyl-17β-methylestra-1,3,5(10)-triene-3-ol, 2-(1-propenyl)-17β-methylestra-1,3,5(10)-triene-3-ol, 2-ethoxy-17β-ethylestra-1,3,5(10)-triene-3-ol, 2-(1-propynyl)-17β-ethylestra-1,3,5(10)-triene-3-ol, 2-formyl-17β-ethylestra-1,3,5(10)-triene-3-ol, 2-formamide-17β-ethylestra-1,3,5(10)-triene-3-ol, 2-methylenehydroxy-17β-ethylestra-1,3,5(10)-triene-3-ol, 2-ethyl-17β-ethylestra-1,3,5(10)-triene-3-ol, 2-methyl-17β-ethylestra-1,3,5(10)-triene-3-ol, 2-(1-propenyl)-17β-ethylestra-1,3,5(10)-triene-3-ol, 2-ethoxy-17(20)-propyleneestra-1,3,5(10)-triene-3-ol, 2-(1-propynyl)-17(20)-propyleneestra-1,3,5(10)-triene-3-ol, 2-formyl-17(20)-propyleneestra-1,3,5(10)-triene-3-ol, 2-formamide-17(20)-propyleneestra-1,3,5(10)-triene-3-ol, 2-methylenehydroxy-17(20)-propyleneestra-1,3,5(10)-triene-3-ol, 2-ethyl-17(20)-propyleneestra-1,3,5(10)-triene-3-ol, 2-methyl-17(20)-propyleneestra-1,3,5(10)-triene-3-ol, 2-(1-propenyl)-17(20)-propyleneestra-1,3,5(10)-triene-3-ol, 2-methoxy-17β-methylenehydroxyestra-1,3,5(10)-triene-3-ol, 2-methoxy-17β-(carboxyliacid)-estra-1,3,5(10)-triene-3-ol, colchicine, combretastatin A-4, diethylstilbestrol, 2-bromoestradiol, 2-methoxyestrone, 2-hydroxyestradiol, 4-hydroxyestradiol, 17-ethynylestradiol, 2-fluoroestradiol, estradiol, estrone, 2-methoxy-17-ethynylestradiol, estriol, 2-methoxyestriol, estradiol-3-O-methyl ether, 2-methoxyestradiol-3-O-methyl ether, 4-methoxyestradiol, 4-methoxestradiol-3-O-methyl ether, podophyllotoxin, dihydrocombretastatin A-4, 3-benzyl-2-methoxyestradiol, 3-benzyl-2-methoxyestrone, 16α-alkyl-3-benzyl-2-methoxyestrone, 16β-alkyl-3-benzyl-2-methoxyestrone, 16-alkyl-16-carbomethoxy-3-benzyl-2-methoxyestrone, 16-methane-dimethylamine-3-benzyl-2-methoxyestrone, 16-carbomethoxy-3-benzyl-2-methoxyestrone, 16-alkyl-3-benzyl-2-methoxyestra-17β-diol, 16-methanol-3-benzyl-2-methoxyestradiol, 16-alkyl-3-benzyl-2-methoxyestradiol, 16β-methyl-2-methoxyestradiol, 16α-methyl-2-methoxyestradiol, 16-ethyl-2-methoxyestradiol, 16α-n-propyl-2-methoxyestradiol, 16β-n-propyl-2-methoxyestradiol, 16β-n-butyl-2-methoxy estradiol, 16β-isobutyl-2-methoxyestradiol, 16β-methyl(dimethyl amine)-2-methoxyestradiol, 16β-methanol-2-methoxyestradiol, 2-Methoxy-17-deoxyestrone, 17-ethyl-2-methoxyestrone, 17-methyl-2-methoxyestrone, 2-N,N-dimethylamino-17-deoxyestrone, 2-Azido-estradiol, and 16α-methanol-2-methoxyestradiol (see e.g., U.S. Pat. No. 6,528,676 and U.S. Patent Application Publication Nos. 2002/0147183 and 2002/0082433).

In certain embodiments, 2-methoxyestradiol, or analogs thereof, and compositions useful in the methods described herein may be supplied, e.g., in a kit, with printed instructions which direct the user to employ the compositions in the methods and for the purposes described herein. The instructions for use may be printed on a container housing the composition or on a separate sheet which is included with the composition. Among other things, the instructions, may for example, direct the user to employ the composition and may also state that the purpose of such method is to inhibit or otherwise prevent symptoms of, or associated with, a pregnancy disorder, such as, for example, preeclampsia. The instructions may be directed to individuals who may be susceptible to (or predisposed of) a pregnancy disorder and/or to those already diagnosed as having a pregnancy disorder.

Formulation

The compositions described herein may be administered by various means, depending on their intended use, as is well known in the art. For example, if compositions are to be administered orally, they may be formulated as tablets, capsules, granules, powders or syrups. Alternatively, formulations may be administered parenterally as injections (intravenous, intramuscular, transdermal patch, by aerosols or subcutaneous), drop infusion preparations or suppositories. These formulations may be prepared by conventional means, and, if desired, the compositions may be mixed with any conventional additive, such as an excipient, a binder, a disintegrating agent, a lubricant, a corrigent, a solubilizing agent, a suspension aid, an emulsifying agent or a coating agent.

In formulations described herein, wetting agents, emulsifiers and lubricants, such as sodium lauryl sulfate and magnesium stearate, as well as coloring agents, release agents, coating agents, sweetening, flavoring and perfuming agents, preservatives and antioxidants may be present in the formulated agents.

Subject compositions may be suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of composition that may be combined with a carrier material to produce a single dose vary depending upon the subject being treated, the severity of the pregnancy disorder, the medication status, and the particular mode of administration.

Methods of preparing these formulations include the step of bringing into association compositions described herein with the carrier and, optionally, one or more accessory ingredients. In general, the formulations are prepared by uniformly and intimately bringing into association agents with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia), each containing a predetermined amount of a subject composition thereof as an active ingredient. Compositions described herein may also be administered as a bolus, electuary, or paste.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds or absorption descelerators, such as cristaline formulas; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art.

Liquid dosage forms for oral administration include pharmaceutically acceptable emulsions, microemulsions, solutions, suspensions, syrups and elixirs. In addition to the subject composition, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Suspensions, in addition to the subject composition, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent. Formulations which are suitable for vaginal administration also include pessaries, tampons, creams, gels, pastes, foams or spray formulations containing such carriers as are known in the art to be appropriate.

Dosage forms for transdermal administration of a subject composition includes powders, sprays, ointments, pastes, creams, lotions, gels, solutions, patches and inhalants. The active component may be mixed under sterile conditions with a pharmaceutically acceptable carrier, and with any preservatives, buffers, or propellants which may be required.

The ointments, pastes, creams and gels may contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a subject composition, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Compositions and compounds described herein may alternatively be administered by aerosol. This is accomplished by preparing an aqueous aerosol, liposomal preparation or solid particles containing the compound. A non-aqueous (e.g., fluorocarbon propellant) suspension could be used. Sonic nebulizers may be used because they minimize exposing the agent to shear, which may result in degradation of the compounds contained in the subject compositions.

Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions that may be suitable for parenteral administration comprise a subject composition in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions described herein include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity may be maintained, for example, by the use of coating materials, such as lecithin, by the maintenance of the required particle size in the case of dispersions, and by the use of surfactants.

In certain embodiments, the subject compounds may be formulated as a tablet, pill capsule or other appropriate ingestible formulation (collectively hereinafter "tablet"), to provide a therapeutic dose in 10 tablets or fewer. In another example, a therapeutic dose is provided in 50, 40, 30, 20, 15, 10, 5 or 3 tablets.

In a certain embodiment, 2-methoxyestradiol, or an analog thereof, is formulated for oral administration as a tablet or an aqueous solution or suspension. A tablet form of 2-methoxyestradiol, or an analog thereof, may be formulated such that the amount of 2-methoxyestradiol, or an analog thereof (or combinations thereof), provided in 20 tablets, if taken together, would provide a dose of at least the median effective dose ($ED_{50}$), e.g., the dose at which at least 50% of individuals exhibited the quantal effect of reduction in at least one symptom associated with a pregnancy disorder. In a further embodiment, the tablets are formulated such that the total amount of 2-methoxyestradiol, or an analog thereof (or combinations thereof), provided in 10, 5, 2 or 1 tablets would provide at least an $ED_{50}$ dose to a patient (human or non-human mammal). In other embodiments, the amount of 2-methoxyestradiol, or an analog thereof (or combinations thereof), provided in 20, 10, 5 or 2 tablets taken in a 24 hour time period would provide a dosage regimen providing, on average, a mean plasma level of the 2-methoxyestradiol, or an analog thereof (or combinations thereof), of at least the $ED_{50}$ concentration. In other embodiments less than 100 times, 10 times, or 5 times the $ED_{50}$ is provided. In other embodiments, a single dose of tablets (1-20 tablets) provides about 0.25 mg to 1250 mg of 2-methoxyestradiol, or an analog thereof (or combinations thereof). In an exemplary embodiment, a single dose of tablets (1-20 tablets) provides about 0.5 to 5 mg, about 1 to about 3 mg, or about 2.5 mg of 2-methoxyestradiol, or an analog thereof (or combinations thereof). Also suitable for oral administration are suspensions and solutions, optionally in association with a sweetened vehicle (such as, for example, a syrup or elixir). The suspension or solution may be formulated at a particular concentration and supplied with a measuring/administering apparatus such as, for example, a spoon or pipette, so that each unit does, e.g., each milliliter, teaspoon, tablespoon, etc. of liquid may contain, for example, about 0.25 mg to 1250 mg of 2-methoxyestradiol, or an analog thereof (or combinations thereof).

Likewise, 2-methoxyestradiol, or an analog thereof, can be formulated for parenteral administration, as for example, for subcutaneous, intramuscular or intravenous injection, e.g., 2-methoxyestradiol, or an analog thereof, can be provided in a sterile solution or suspension (collectively hereinafter "injectable solution"). The injectable solution is formulated such that the amount of 2-methoxyestradiol, or an analog thereof (or combinations thereof), provided in a 200 cc bolus injection would provide a dose of at least the median effective dose, or less than 100 times the $ED_{50}$, or less than 10 or 5 times the $ED_{50}$. The injectable solution may be formulated such that the total amount of 2-methoxyestradiol, or an analog thereof (or combinations thereof), provided in 100, 50, 25, 10, 5, 2.5, or 1 cc injections would provide an $ED_{50}$ dose to a patient, or less than 100 times the $ED_{50}$, or less than 10 or 5 times the $ED_{50}$. In other embodiments, the amount of 2-methoxyestradiol, or an analog thereof (or combinations thereof), provided in a total volume of 100 cc, 50, 25, 5 or 2 cc to be injected at least twice in a 24 hour time period would provide a dosage regimen providing, on average, a mean plasma level of the 2-methoxyestradiol, or an analog thereof (or combinations thereof), of at least the $ED_{50}$ concentration, or less than 100 times the $ED_{50}$, or less than 10 or 5 times the $ED_{50}$. In other embodiments, a single dose injection provides about 0.25 mg to 1250 mg of 2-methoxyestradiol, or an analog thereof (or combinations thereof). In an exemplary embodiment, a single dose injection provides about 0.5 to 5 mg, about 1 to about 3 mg, or about 2.5 mg of 2-methoxyestradiol, or an analog thereof (or combinations thereof).

EXEMPLIFICATION

The invention now being generally described, it will be more readily understood by reference to the following examples which are included merely for purposes of illustration of certain aspects and embodiments of the present invention, and are not intended to limit the invention in any way.

Angiogensis plays an important role in the individual development and construction of tissues in vertebrates, including formation of the corpus luteum during the sexual cycle, transient proliferation of the uterine endometrium, and formation of the placenta in mature individuals (females). Additionally, angiogenesis is important during pregnancy for normal fetal development. During pregnancy, cytotrophoblasts are converted from an epithelial to an endothelial phenotype (a process referred to as pseudo-vasculogenesis) and invade maternal spiral arteries. This vascular remodeling is necessary to increase the supply of nutrients and oxygen to the fetus by the end of the first trimester. When pseudovasculogenesis is defective, preeclampsia develops and the placenta becomes ischemic.

Angiogenesis is stimulated by the secretion of an angiogenesis factor and results in the production of new blood vessels. During this process, the basement membrane and interstitum are destroyed by a protease secreted from endothelial cells of an existing blood vessel around the secreted angiogenesis factor, followed by subsequent wandering and proliferation of vascular endothelial cells (J. Biol. Chem., 267, 10931, (1992)). One of the key factors involved in the induction of angiogenesis is vascular endothelial growth factor, or VEGF. VEGF has been shown to have a variety of activities including an angiogenesis enhancing activity (Circulation, 92 suppl II, 365 (1995)) and a vascular permeability enhancing activity (Science, 219, 983 (1983)).

Flt-1 (fms-like tyrosine kinase 1) is one of the two receptors for vascular endothelial growth factor (VEGFR-1); the other being KDR (VEGFR-2, Flk-1). The Flt-1 protein consists of an external domain containing seven immunoglobulin like domains, a transmembrane region, and a cytoplasmic region containing a tyrosine kinase domain. In contrast to other members of the receptor tyrosine kinase family, the kinase domain of flt-1 is in two segments with an intervening sequence of about 70 amino acids. The biology of the VEGF receptors has been reviewed (Neufeld et al., (1999) FASEB Journal. 13:11-22; Zachary (1998) Experimental Nephrology. 6:480-487) and the tyrosine phosphorylation sites have been identified (Ito et al., (1998) J. Biol. Chem. 273:23410-23418). It is thought that flt-1 may be important in regulating the tissue architecture in developing vasculature while the second VEGF receptor (KDR, VEGFR-2, Flk-1) mediates the mitogenic and angiogenic effects of VEGF in endothelial cells. Evidence to support this theory has come from knockout studies in mice (Fong et al., (1995) Nature. 376:66-70). Additional studies have also shown that expression of Flt-1, but not Flk-1/KDR, is upregulated by hypoxia and HIF-1α in human umbilical vein endothelial cells.

Soluble Flt-1 (sFlt-1), a splice variant of Flt-1, lacks the transmembrane and cytoplasmic domains of Flt-1 and has been shown to act as a potent antagonist of VEGF and PlGF (placental growth factor). When Flt-1 binds to VEGF and PlGF it transmits an angiogenic signal, however, sFlt-1 is not capable of transmitting the signal because it lacks a cytoslic domain. Accordingly, sFlt-1 functions by regulating (reducing) the levels of free VEGF and PlGF available to signal via intact Flt-1. Recently it has been shown that sFlt-1 is upregulated in subjects suffering from preeclampsia. It has been hypothesized that high levels of sFlt-1 lead to placental vascular insufficiency by antagonizing the angiogenic and vasodilatory effects of VEGF and PlGF. However, the level of sFlt-1 alone does not seem to be enough to explain the development of preeclampsia as some women with high sFlt-1 levels do not develop preeclampsia whereas some women with low levels of sFlt-1 do develop preeclampsia.

Hypoxia-Inducible Factor 1 (HIF-1) is a transcription factor that has been shown to play an essential role in cellular responses to hypoxia. Upon hypoxic stimulation, HIF-1 has been shown to activate genes that contain Hypoxic Response Elements (HREs) in their promoters, and thus up-regulate a series of gene products that promote cell survival under conditions of low oxygen availability. The list of HIF-responsive genes is constantly expanding, but known gene products include glycolytic enzymes (such as lactate dehydrogenase (LDH-A), enolase-1 (ENO-1), and aldolase A), glucose transporters (GLUT 1 & 3), vascular endothelial growth factor (VEGF), inducible nitric oxide synthase (NOS-2), and erythropoietin (EPO). The switch of the cell to anaerobic glycolysis, and the up-regulation of angiogenesis by VEGF is geared at maximizing cell survival under conditions of low oxygen tension by reducing the requirement for oxygen, and increasing vasculature to maximize oxygen delivery to tissues.

The HIF-1 transcription complex has recently been shown to comprise a heterodimer of two basic helix-loop-helix proteins, HIF-1α and HIF-1β (also known as ARNT, Aryl Hydrocarbon Receptor Nuclear Translocator). HIF-1α is a member of the basic-helix-loop-helix PAS domain protein family and is an approximately 120 kDa protein containing two transactivation domains (TAD) in its carboxy-terminal half and DNA binding activity located in the N-terminal half of the molecule. HIF-1α is constitutively degraded by the ubiquitin-proteosome pathway under conditions of normoxia, a process that is facilitated by binding of the von Hippel-Lindau (VHL) tumor suppressor protein to HIF-1α. Under conditions of hypoxia, degradation of HIF-1α is blocked and active HIF-1α accumulates. The subsequent dimerization of HIF-1α with ARNT leads to the formation of active HIF transcription complexes in the nucleus, which can bind to and activate HREs on HIF-responsive genes.

2-Methoxyestradiol (2-ME) is an endogenous metabolite of estradiol (E2) that has potent anti-proliferative activity and induces apoptosis in a wide variety of tumor and non-tumor cell lines. When administered orally, it exhibits antitumor and antiangiogenic activity with little or no toxicity. Currently, 2-ME is in several phase-I and II clinical trials for cancer therapies under the name PANZEM™. 2-ME has been shown to downregulate HIF-1 at the posttranscriptional level and inhibits HIF-1 induced transcriptional activation of VEGF expression. An illustration of some of the proteins that may be involved in this process is shown in FIG. 1.

We have now discovered that 2-methoxyestradiol (2-ME), a natural metabolite of estradiol, may be used as a therapeutic agent for preeclampsia and other pregnancy related disorders which are associated with high expression of sFLT-1 which reduces the levels of free VEGF. Blocking of circulating VEGF leads to proteinuria (Sugimoto et al., J. Biol. Chem. (2003) 278:12605-8). 2-methoxyestradiol is significantly decreased (up to 6-7 fold) in the circulation of pregnant women with preeclampsia in the second and third trimesters of pregnancy as compared to non-preeclamptic women. 2-methoxyestradiol decreases the expression of HIF-1α in cytotrophoblasts from the placenta which leads to a dramatic decrease in the expression of VEGF, PlGF, VEGF Receptor 1 (VEGFR1) and sFLT-1.

Example 1

Figure 2:
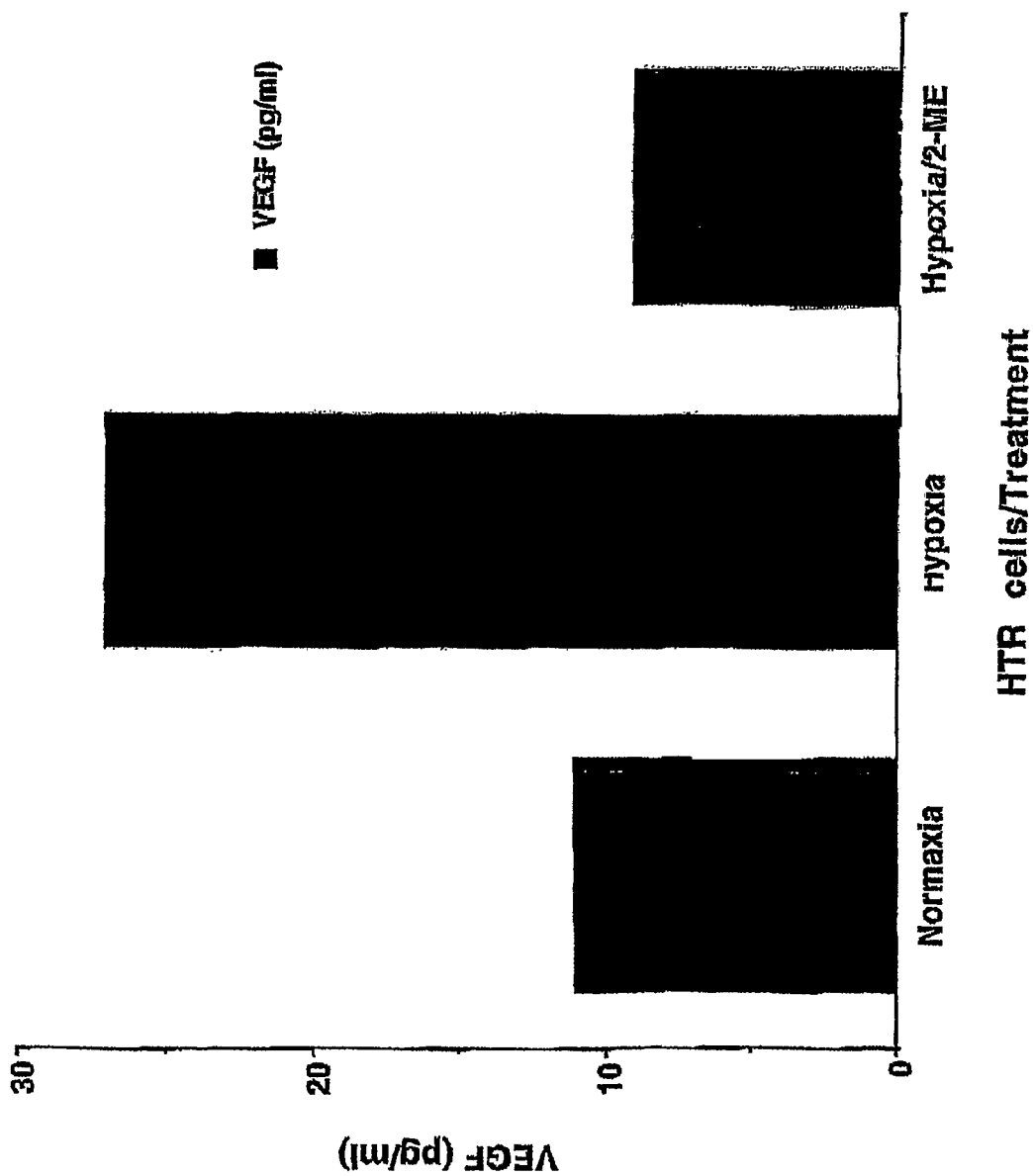
FIG. 2 is a graph showing that 2-methoxyestradiol treatment of HTR cytotrophoblasts under hypoxia reduces secretion of VEGF.
Figure 3:
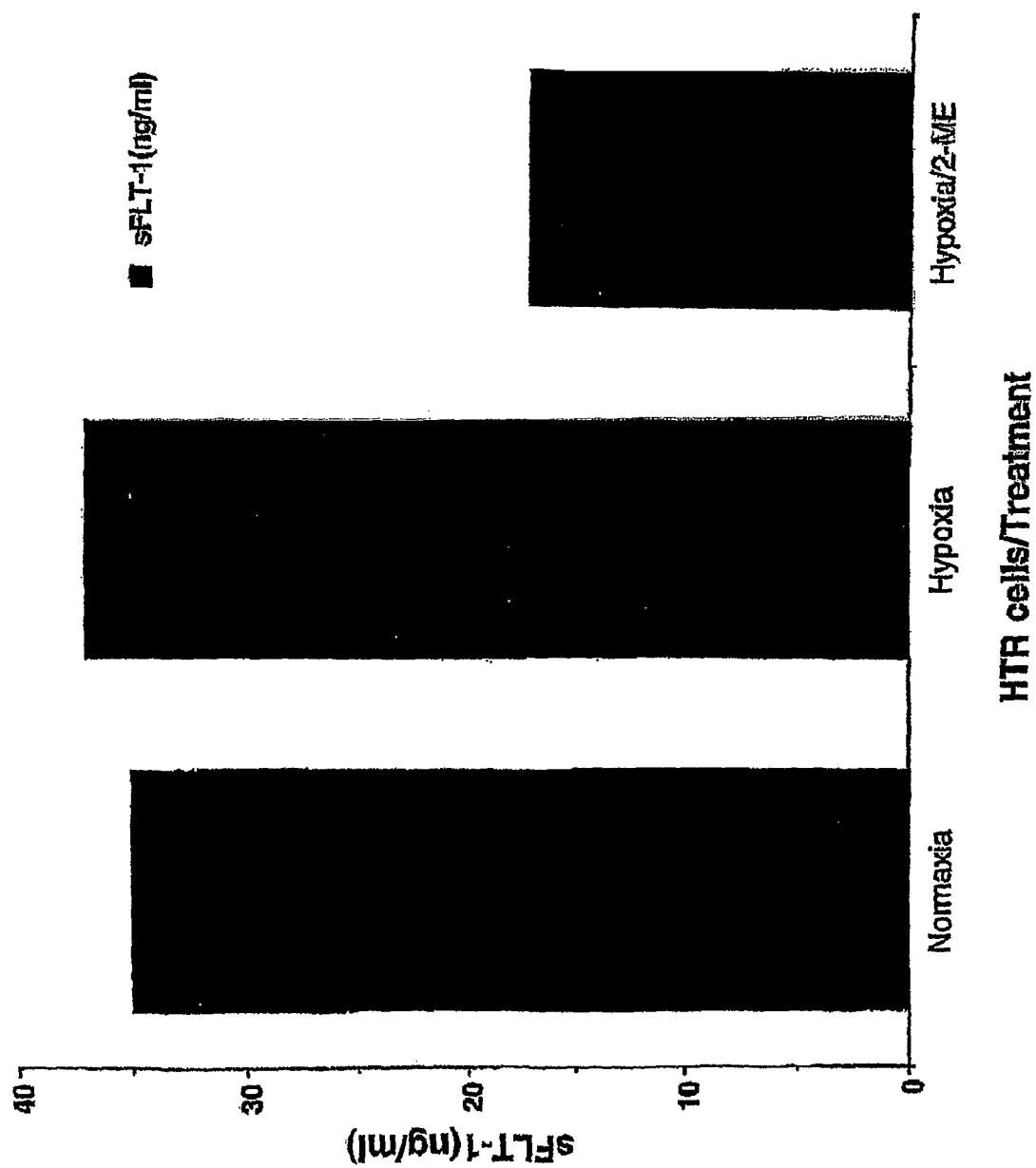
FIG. 3 is a graph showing that 2-methoxyestradiol treatment of HTR cytotrophoblasts leads to reduction of sFLT-1 production.
Figure 4:
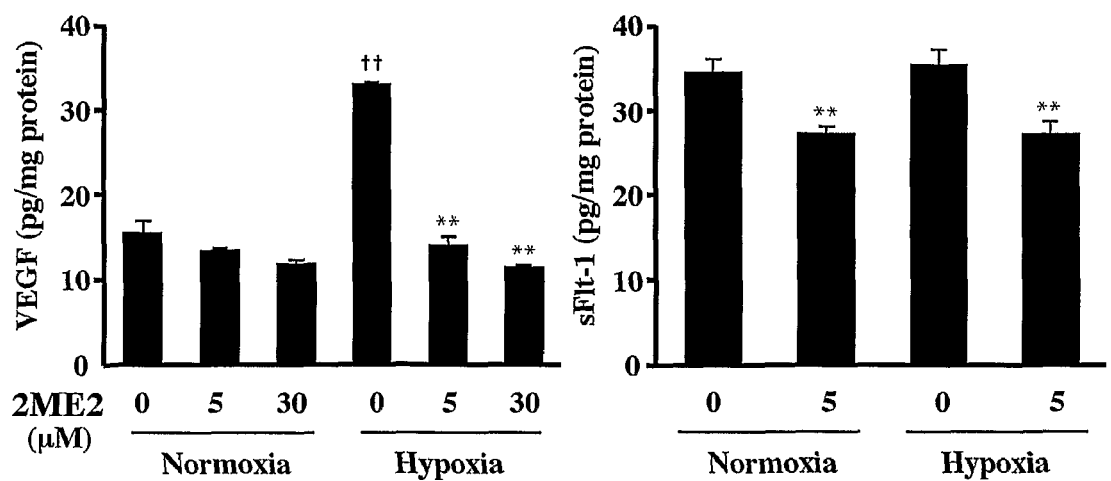
FIG. 4 is a graph showing that 2-methoxyestradiol treatment of HTR-8/SV neo trophoblast cells leads to a reduction of VEGF and sFlt-1 secretion.
Figure 5:
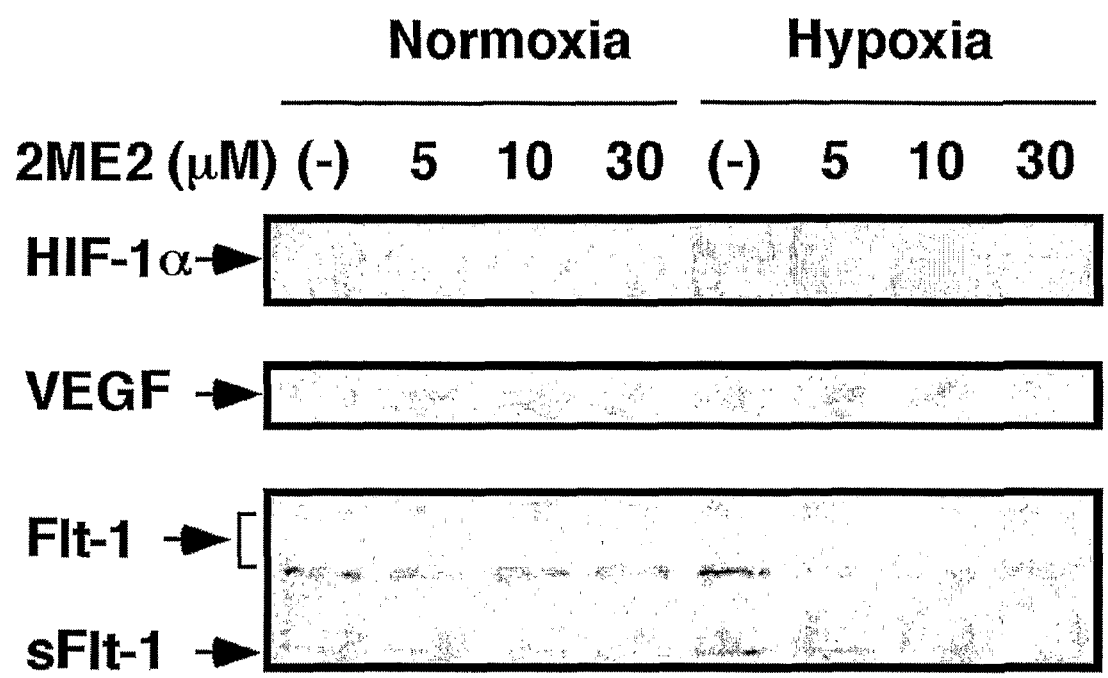
FIG. 5 is a blot showing that 2-methoxyestradiol treatment of HTR-8/SV neo trophoblast cells downregulations HIF-1α, $VEGF_{165}$, Flt-1, and sFlt-1 expression in cell lysates under hypoxic conditions.

2-Methoxyestradiol Treatment Reduces Expression of VEGF, sFlt-1 and HIF-1α in Tissue Culture Cells We have shown that 5 μM, 10 μM and 30 μM of 2-ME can reduce the secreted levels of VEGF up to 75% in a dose dependent manner in a placenta cytotrophoblast cell line (HTR) under hypoxia. Similar results are also seen when a different cytotrophoblast cell line (BeWo cells) is used. Similarly, 5 μM, 10 μM and 30 μM of 2-ME can reduce the secreted sFLT-1 levels by up to 50% or more in a dose dependent manner in the same cell lines under hypoxia (see FIGS. 1-3). Expression levels of HIF-1α, VEGF$_{165}$, Flt-1 and sFlt-1 in trophoblast cell lysates are downregulated at 5 μM, 10 μM and 30 μM of 2-ME under hypoxic conditions (see FIG. 4). Further, 5 μM, 10 μM and 30 μM of 2-ME can reduce PlGF secretion levels in a dose dependent manner in the same cell lines under hypoxia (see FIG. 5).

Example 2

2-Methoxyestradiol Treatment of Mice Reduces Expression of sFLT-1 and Bound VEGF in Vivo Normal mice were treated with 2-ME twice daily with 30 μM of 2-ME. Blood samples were then obtained and assayed for the level of sFLT-1 and VEGF. The mice showed a 50% reduction in sFLT-1 expression and a decrease in bound VEGF. The 30 μM concentration represents approximately the normal physiological level of 2-ME that is found in the blood of pregnant women in the late second trimester or early third trimester through the end of pregnancy. At the end of a pregnancy, levels of 2-ME in non-preeclamptic subjects drops back to non pregnant levels, which are approximately 1-5 µM.

Example 3

Figure 6:
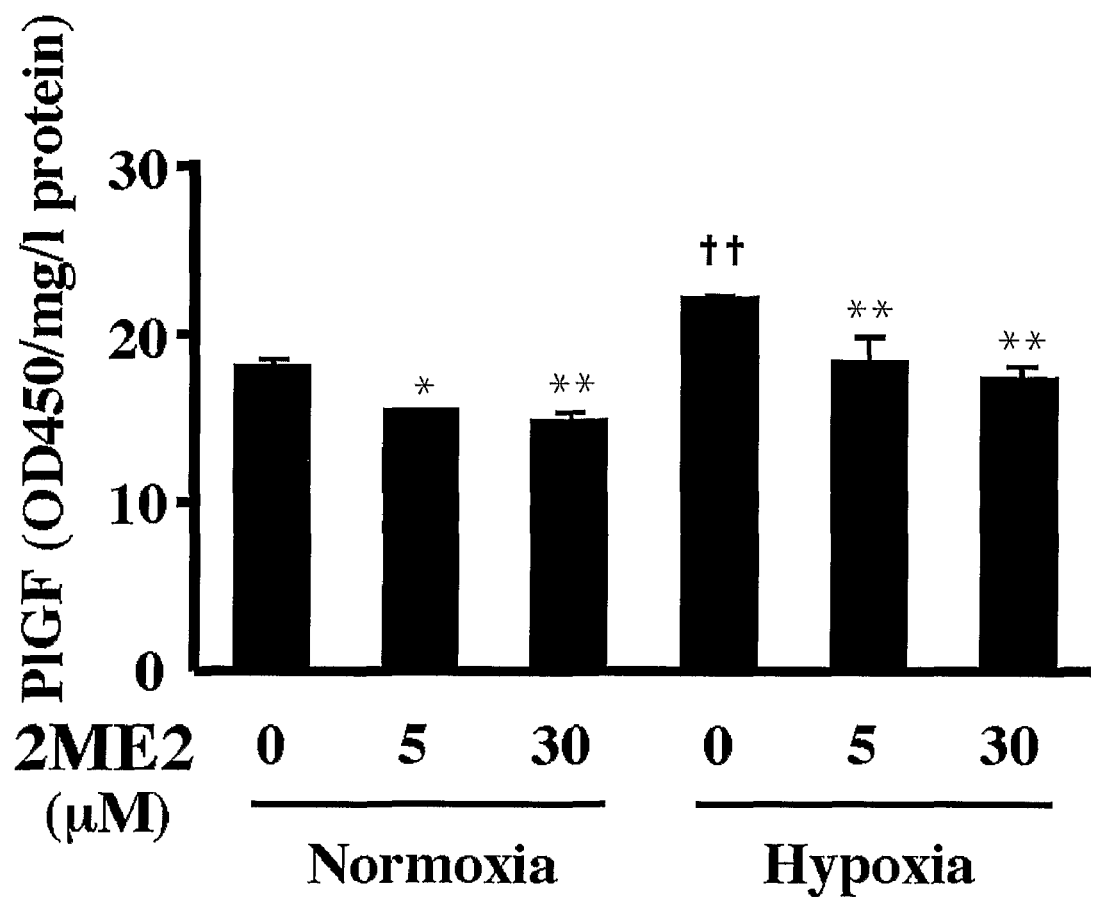
FIG. 6 is a graph showing that 2-methoxyestradiol treatment of HTR-8/SV neo trophoblast cells leads to a reduction of PlGF secretion.
Figure 7:
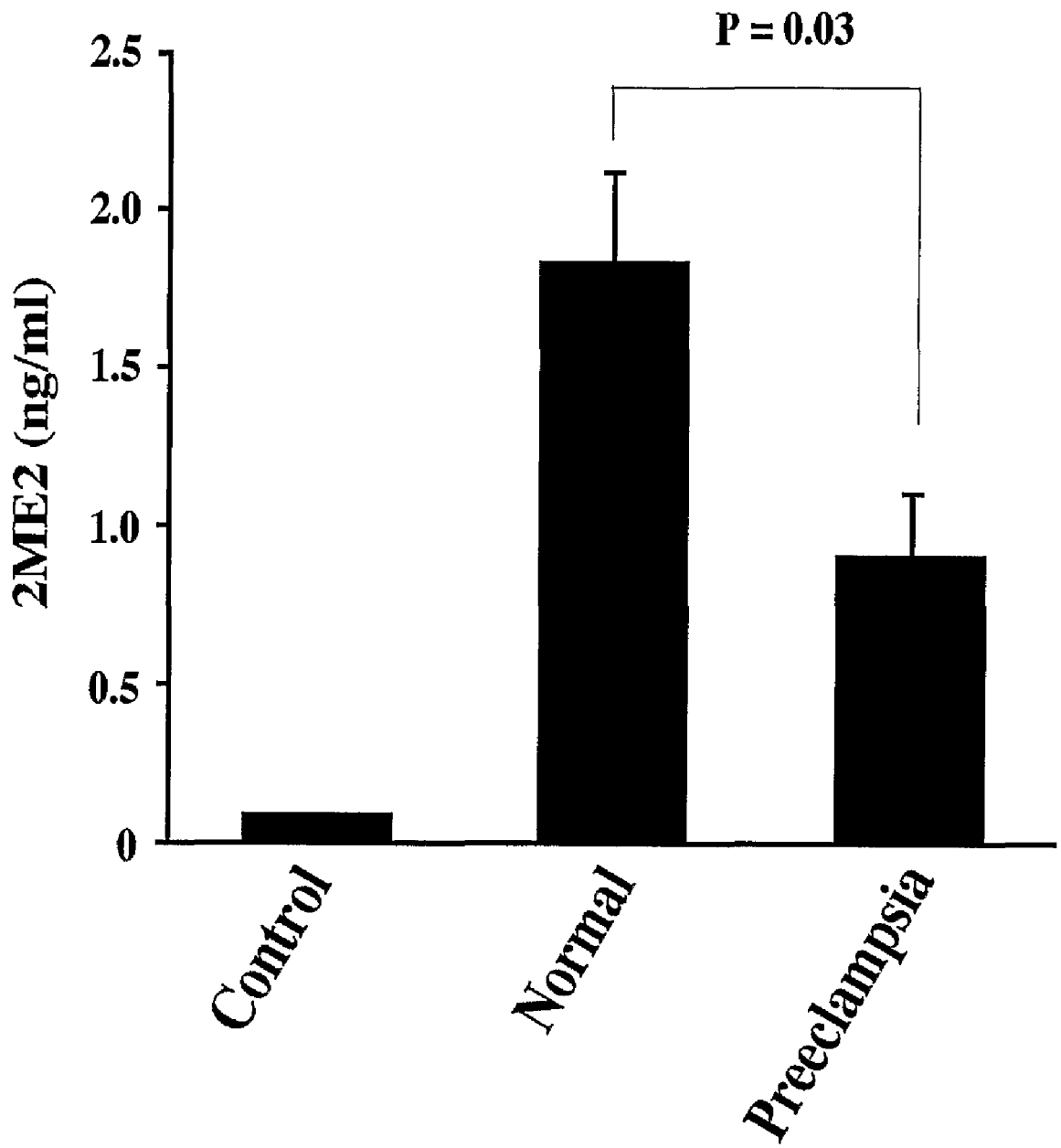
FIG. 7 is a graph showing that the concentration of of 2-methoxyestradiol is decreased in sera from preclampsia.

Levels of 2-Methoxyestradiol are Lower in Preeclamptic Subjects as Compared to Control Subjects The levels of 2-methoxyestradiol from urine and blood samples of pregnant women suffering from preeclampsia were compared with the levels in control subjects (e.g., pregnant women not suffering from preeclampsia). The concentration of 2-methoxyestradiol is decreased in sera from preclampsia (see FIG. 6). The observed decrease in 2-methoxyestradiol is statistically signficant with a p value of 0.03.

EQUIVALENTS

The present disclosure provides among other things methods and compositions for treating hypertension. While specific embodiments have been discussed, the above specification is illustrative and not restrictive. Many variations of the methods, compositions, and process disclosed herein will become apparent to those skilled in the art upon review of this specification. The appended claims are not intended to claim all such embodiments and variations, and the full scope of the invention should be determined by reference to the claims, along with their full scope of equivalents, and the specification, along with such variations.

INCORPORATION BY REFERENCE

All publications and patents mentioned herein, including those items listed below, are hereby incorporated by reference in their entirety as if each individual publication or patent was specifically and individually indicated to be incorporated by reference. In case of conflict, the present application, including any definitions herein, will control.

Also incorporated by reference are the following: U.S. Pat. Nos. 6,528,676; 6,613,757; 6,086,865; 5,892,069; 5,661,143; 5,504,074; 5,198,366; and 5,849,474; U.S. Patent Application Publication Nos.: 2003/0236439; 2003/0187076; 2002/0147183; 2003/0236408; 2003/0195180; 2003/0096800; 2003/0055029; 2002/0165212; 2002/0082433; 2004/0018201; 2002/0102530; and 2002/0119959; WO 03/015704; Semenza, Genes Dev. 14: 1983-1991 (2000); Takanashi et al., Lipids 38(8): 847-854(2003); Takanashi et al., Clinical Chemistry 46(3): 373-378 (2000); Solomon et al., N Eng. J. Med. 3 50(7): 641-642 (2004); Levine et al., N Eng. J. Med. 350(7): 672-683 (2004); Maynard et al., S. Clin. Invest. 111(5): 649-658 (2003); Luttun and Carmeliet, J. Clin. Invest. 111(5): 600-602 (2003); Hosford and Olson, Am. J. Physiol. 285: L161-L168 (2003); D'Amato et al., Proc. Natl. Acad. Sci. USA 91: 3964-3968 (1994); Semenza, J. Clin. Invest. 106(7): 809-812 (2000); D'Amato et al., Proc. Natl. Acad. Sci. USA 91: 4082-4085 (1994); Evans et al., Clin. Sci. 92(6):567-71 (1997); Gerber et al., J. Biol. Chem. 272(38): 23659-67 (1997); Rivard et al., J. Biol. Chem. 275: 29643-29647 (2000); Semenza, Cancer Metastasis Rev. 19(1-2): 59-65 (2000); Mabjeesh et al., Cancer Cell. 3(4): 363-75 (2003); Kieran et al., Nat. Med. 9(9): 1104 (2003); Mooberry, Curr. Opin. Oncol. 15(6): 425-30 (2003); Sharkey et al., Eur. J. Clin. Invest. 26 (12):1182-5 (1996); Sugimoto et al., J. Biol. Chem. 278(15):12605-8 (2003); and Zagzag et al., Cancer 88(11): 2606-18 (2000).

We claim:

1. A method for treating preeclampsia comprising administering to a pregnant subject in need thereof an effective amount of 2-methoxyestradiol (2-ME), or a pharmaceutically acceptable salt thereof.

2. The method of claim 1, wherein the method further comprises determining the level of 2-methoxyestradiol in a biological sample from said subject.

3. The method of claim 2, wherein the level of 2-methoxyestradiol is determined by determining the level of a estradiol, 2-hydroxyestradiol, or 2 methoxyestrone.

4. The method of claim 2, wherein the method further comprises comparing said level of 2-methoxyestradiol to the level of 2-methoxyestradiol in a control.

5. The method of claim 1, wherein the method further comprises determining the level of estradiol or 2-hydroxyestradiol in a biological sample from said subject.

6. The method of claim 5, wherein the method further comprises comparing said level of estradiol or 2-hydroxyestradiol to the level of estradiol or 2-hydroxyestradiol in a control.

7. The method of claim 1, wherein the method further comprises determining the level of 2-methoxyestrone in a biological sample from said subject.

8. The method of claim 7, wherein the method further comprises comparing said level of 2 methoxyestrone to the level of 2 methoxyestrone in a control.

9. The method of claim 2, wherein said biological sample is urine, blood or plasma.

10. The method of claim 2, wherein said control is a predetermined standard from at least one non-preeclamptic subject at about the same stage of pregnancy as said subject.

11. The method of claim 4, wherein if the level of 2-methoxyestradiol in said subject sample is lower than the level of 2-methoxyestradiol in said control, the method further comprises administering to said subject an amount of 2-methoxyestradiol, effective to increase the level of 2-methoxyestradiol in said subject to a level that is about the same as the level of 2-methoxyestradiol in said control.

12. The method of claim 4, wherein the method comprises determining the level of 2-methoxyestradiol in said subject as compared to a control on a regular basis.

13. The method of claim 12, wherein said regular basis is once about every 1, 2, 3, 4, 5, 6, 7, 10, 14, 28, or 35 days.

14. The method of claim 12, which further comprises adjusting the level of 2-methoxyestradiol, administered to said subject on a regular basis so that the level of 2-methoxyestradiol thereof is maintained in said subject at a level that is about the same as the level of 2-methoxyestradiol in a control.

15. The method of claim 1, wherein said subject is a human.

16. The method of claim 1, wherein about 0.1, 0.3, 1, 2.5, or 5 mg of said 2-methoxyestradiol, is administered to said subject.

17. The method of claim 1, wherein said 2-methoxyestradiol, is administered orally, nasally, parenterally or transdermally.

18. The method of claim 1, which further comprises monitoring said subject for one or more symptoms of preeclampsia.

19. The method of claim 18, wherein said symptoms of preeclampsia include one or more of the following: elevated maternal blood pressure, proteinuria, headache, visual disturbances, upper abdominal pain, oliguria, serum creatinine, thrombocytopenia, hyperbilirubinemia, liver enzyme elevation, pulmonary edema, pulmonary distress, convulsions, or fetal growth retardation.

20. The method of claim 19, wherein the blood pressure of said subject is monitored on a regular basis.

21. The method of claim 20, wherein a regular basis is at least once a week.

22. The method of claim 21, wherein a regular basis is at least once a day.

23. The method of claim 1, which further comprises administering to said subject an anti-hypertensive agent.

24. The method of claim 23, wherein said anti-hypertensive agent is one or more of the following: hydralazine, labetalol, or nitroprusside.

25. The method of claim 23, wherein said anti-hypertensive agent is administered to said subject concurrently with said 2-methoxyestradiol, or pharmaceutically acceptable salt thereof.

26. The method of claim 1, which further comprises administering to said subject an anti-convulsant agent.

27. The method of claim 26, wherein said anti-convulsant agent is one or more of the following: magnesium sulfate, phenytoin, or diazepam.

28. The method of claim 26, wherein said anti-convulsant agent is administered to said subject concurrently with said 2-methoxyestradiol, or pharmaceutically acceptable salt thereof.

29. The method of claim 1, which further comprises administering to said subject an anti-hypertensive agent and an anti-convulsant agent.

30. A method for treating preeclampsia, comprising:
a) determining the level of 2-methoxyestradiol in a biological sample from a pregnant subject and comparing said level to the level of 2-methoxyestradiol in a control, wherein said control is a predetermined standard from at least one non-preeclamptic subject at about the same stage of pregnancy as said pregnant subject;
b) administering to said pregnant subject an amount of 2-methoxyestradiol, or a pharmaceutically acceptable salt thereof, sufficient to raise the level of 2-methoxyestradiol in a biological sample of said subject to a level that is about the same as the level of 2-methoxyestradiol in said control; and
c) repeating steps a) and b) on a regular basis thereby maintaining the level of 2-methoxyestradiol in said subject at a level that is about the same as the level of 2-methoxyestradiol in the control.

31. The method of claim 30, wherein said biological sample is urine, blood or plasma.

32. A method for reducing placental hypoxia in a subject with preeclampsia comprising administering to the subject an effective amount of 2-methoxyestradiol (2-ME), or a pharmaceutically acceptable salt thereof, to thereby reduce placental hypoxia in the subject.

33. A method for reducing sFLT-1 in a subject with preeclampsia comprising administering to the subject an effective amount of 2-methoxyestradiol (2-ME), or a pharmaceutically acceptable salt thereof, to thereby reduce the sFLT-1 in the subject.

* * * * *